United States Patent  
Das et al.

(10) Patent No.: US 8,384,981 B2
(45) Date of Patent: *Feb. 26, 2013

(54) ELECTROCHROMIC MATERIAL AND ELECTROCHROMIC DEVICE INCLUDING THE SAME

(75) Inventors: Rupasree Ragini Das, Suwon-si (KR); Chang-Ho Noh, Suwon-si (KR); Ji-Min Lee, Hwaseong-si (KR); Seog-Jin Jeon, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 288 days.

This patent is subject to a terminal disclaimer.

(21) Appl. No.: 12/658,835

(22) Filed: Feb. 16, 2010

(65) Prior Publication Data

US 2011/0002027 A1    Jan. 6, 2011

(30) Foreign Application Priority Data

Jul. 2, 2009  (KR) .................. 10-2009-0060388

(51) Int. Cl.
    *G02F 1/15*  (2006.01)
(52) U.S. Cl. ...................................... 359/265
(58) Field of Classification Search .......... 359/265–275; 252/583; 546/22, 256, 258
    See application file for complete search history.

(56) References Cited

U.S. PATENT DOCUMENTS

| 4,960,324 | A * | 10/1990 | Brown ..................... 359/265 |
| 7,342,706 | B2 * | 3/2008 | Shinohara et al. ......... 359/265 |
| 2005/0179012 | A1 | 8/2005 | Kwon et al. |
| 2006/0110638 | A1 | 5/2006 | Corr et al. |
| 2009/0082570 | A1 * | 3/2009 | Nii et al. .................. 546/258 |
| 2009/0130367 | A1 * | 5/2009 | Nii et al. .................. 428/64.8 |

FOREIGN PATENT DOCUMENTS

| JP | 2008-179725 A | 8/2008 |
| WO | 9932926 A1 | 7/1999 |
| WO | 2004067673 A1 | 8/2004 |
| WO | 2005062110 A1 | 7/2005 |
| WO | 2005095342 A1 | 10/2005 |
| WO | 2008146674 A1 | 12/2008 |

* cited by examiner

*Primary Examiner* — Ricky L. Mack
*Assistant Examiner* — Tuyen Tra
(74) *Attorney, Agent, or Firm* — Cantor Colburn LLP

(57) ABSTRACT

An electrochromic material including at least one compound represented by Chemical Formulas 1 to 3, for use in an electrochromic device:

Chemical Formula 1

Chemical Formula 2

-continued

Chemical Formula 3

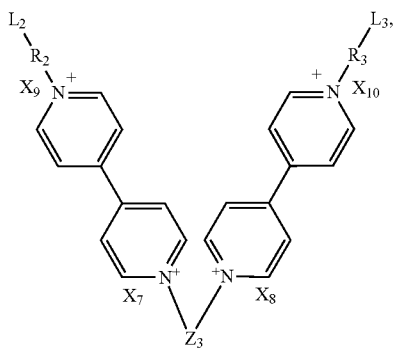

wherein $Z_1$ to $Z_3$ are each independently selected from a substituted or unsubstituted $C_6$ to $C_{30}$ arylene group, a substituted or unsubstituted $C_2$ to $C_{30}$ heteroarylene group, a substituted or unsubstituted $C_3$ to $C_{30}$ cycloalkylene group or a combination thereof, $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof.

19 Claims, 17 Drawing Sheets
(6 of 17 Drawing Sheet(s) Filed in Color)

ELECTROCHROMIC MATERIAL AND ELECTROCHROMIC DEVICE INCLUDING THE SAME

CROSS-REFERENCE TO RELATED APPLICATION

This application claims priority to Korean Patent Application No. 10-2009-0060388, filed on Jul. 2, 2009, and all the benefits accruing therefrom under 35 U.S.C. §119, the contents of which in its entirety is herein incorporated by reference.

BACKGROUND

1. Field

This disclosure relates to an electrochromic material and an electrochromic device including the same.

2. Description of the Related Art

Electrochromism refers to a phenomenon in which a color of a material reversibly changes in response to the direction of an electric field when a voltage is applied. A material, whose optical characteristics may reversibly change through an electrochemical redox reaction, is called an electrochromic material. An electrochromic material may be colorless until an electric field is applied thereto, or conversely it may be colored when no electric field is applied and become colorless when an electric field is applied.

An electrochromic material has been applied to an electrochromic device that changes light transmission characteristics depending on an applied voltage.

An electrochromic device is applicable to a device using light transmission characteristics, such as smart windows. Recently an electrochromic device has also been applied to a display device, such as electronic paper, due to the excellent portability and lightweight characteristics of the electrochromic device.

SUMMARY

An aspect, feature or advantage of an embodiment is a novel electrochromic material.

Another aspect, feature or advantage of an embodiment is an electrochromic device including the electrochromic material.

Disclosed is an electrochromic material including at least one compound represented by Chemical Formulas 1 to 3:

Chemical Formula 1

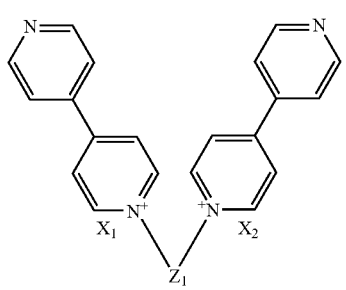

Chemical Formula 2

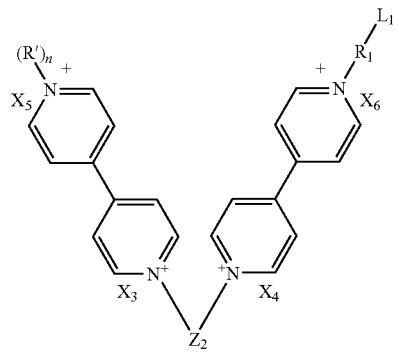

Chemical Formula 3

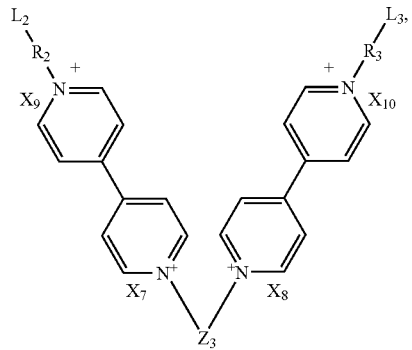

wherein $Z_1$ to $Z_3$ are each independently selected from a substituted or unsubstituted $C_6$ to $C_{30}$ arylene group, a substituted or unsubstituted $C_2$ to $C_{30}$ heteroarylene group, a substituted or unsubstituted $C_3$ to $C_{30}$ cycloalkylene group or a combination thereof, $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group and a hydroxyl group or a combination thereof, and $X_1$ to $X_{10}$ are each independently a halogen group, a halogen-containing group or a combination thereof.

According to another embodiment, disclosed is an electrochromic device, including: a first electrode; a second electrode facing the first electrode; an electrochromic material disposed on either the first electrode or the second electrode; and an electrolyte layer interposed between the first electrode and the second electrode, wherein the electrochromic material includes at least one electrochromic compound represented by the Chemical Formulae 1 to 3:

Chemical Formula 1

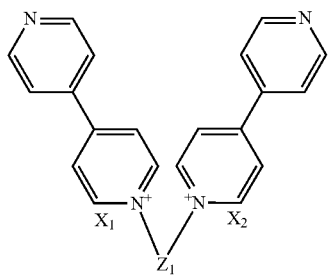

Chemical Formula 2

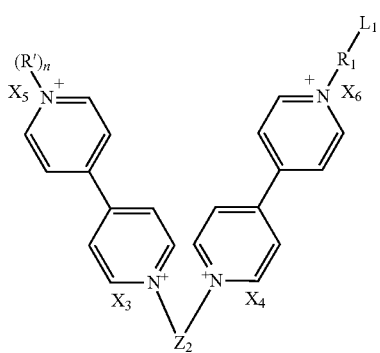

Chemical Formula 3

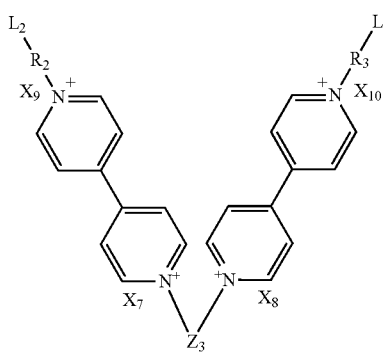

wherein $Z_1$ to $Z_3$ are each independently selected from a substituted or unsubstituted $C_6$ to $C_{30}$ arylene group, a substituted or unsubstituted $C_2$ to $C_{30}$ heteroarylene group, a substituted or unsubstituted $C_3$ to $C_{30}$ cycloalkylene group or a combination thereof, $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group or a hydroxyl group, and $X_1$ to $X_{10}$ are each independently a halogen group, a halogen-containing group or a combination thereof.

In an embodiment, $Z_1$ to $Z_3$ may each independently be a radical of Chemical Formula A:

Chemical Formula A

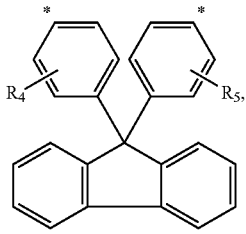

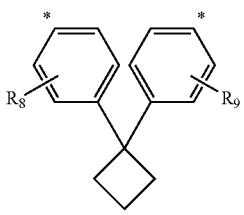 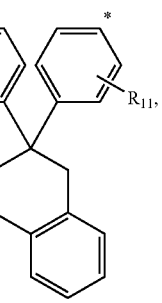

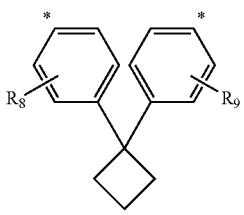 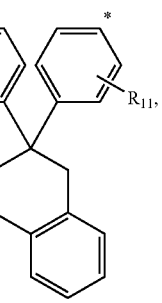

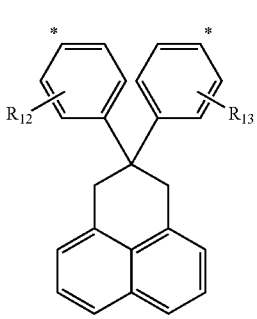

wherein $R_4$ to $R_{13}$ are each independently selected from hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group, a halogen group, a halogen-containing group or a combination thereof, and * represents a point of attachment.

The compound may express green.

The compound represented by Chemical Formula 1 may include at least one compound of Chemical Formulas 1A to 1C, the compound represented by Chemical Formula 2 includes at least one compound of Chemical Formulas 2A to 2C, and the compound represented by Chemical Formula 3 includes at least one compound of Chemical Formulas 3A to 3E:

Chemical Formula 1A
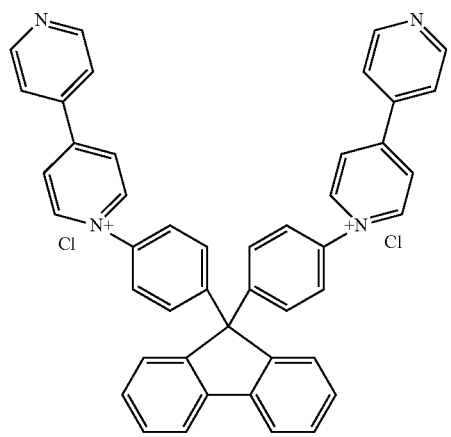
Chemical Formula 1B
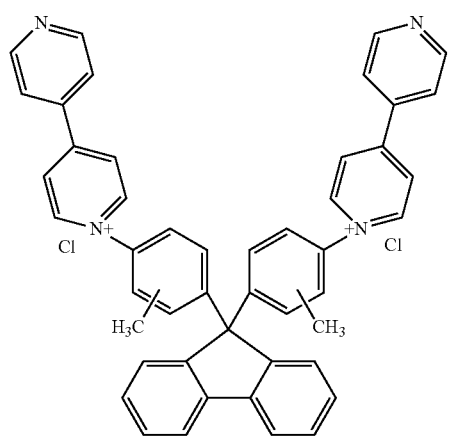
Chemical Formula 1C
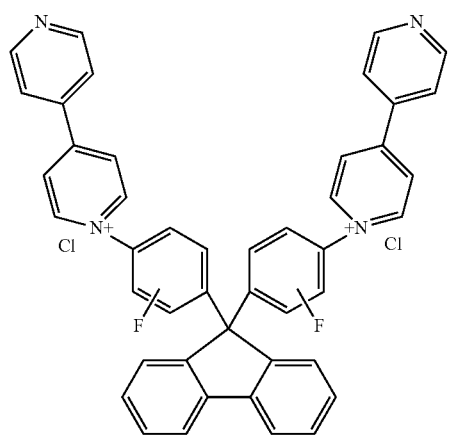
-continued
Chemical Formula 2A
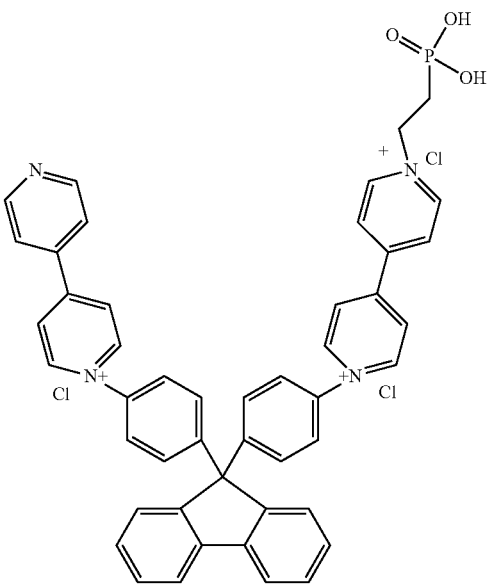
Chemical Formula 2B
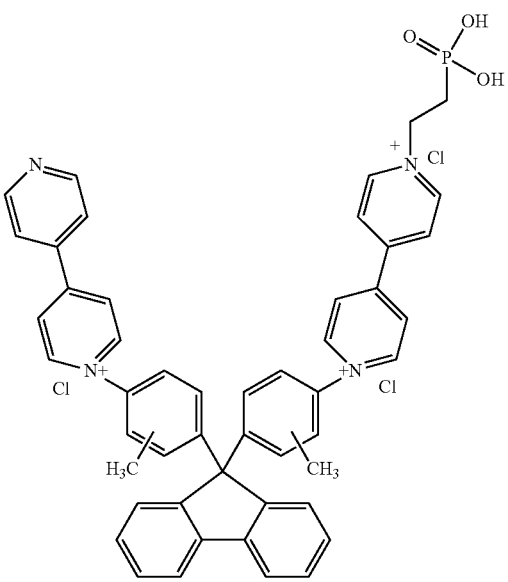

Chemical Formula 2C
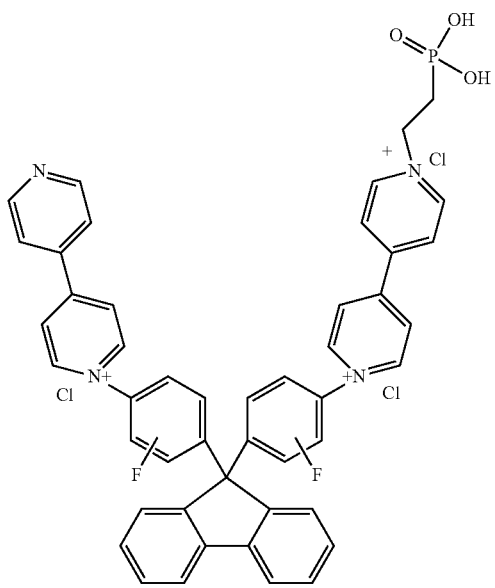
Chemical Formula 3A
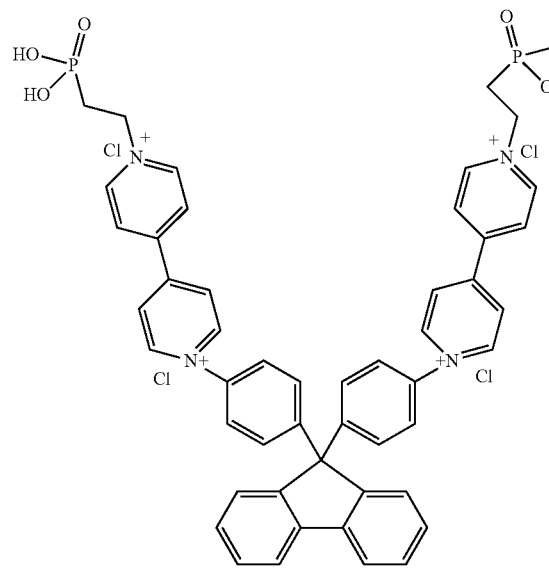
Chemical Formula 3B
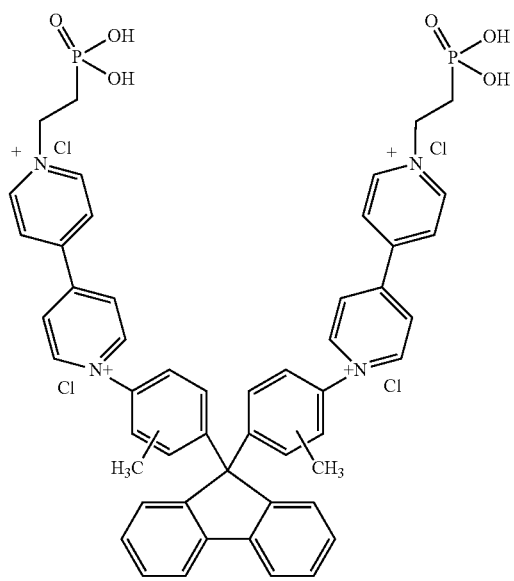
Chemical Formula 3C
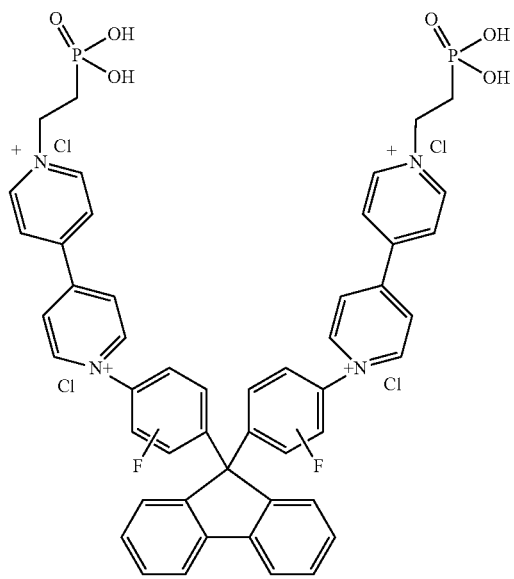

Chemical Formula 3D

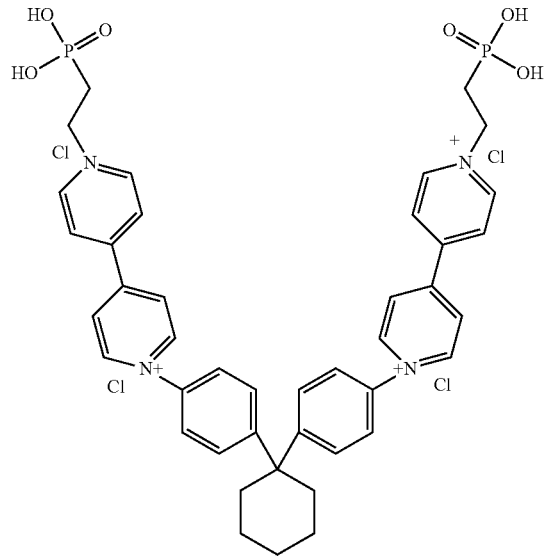

Chemical Formula 3E

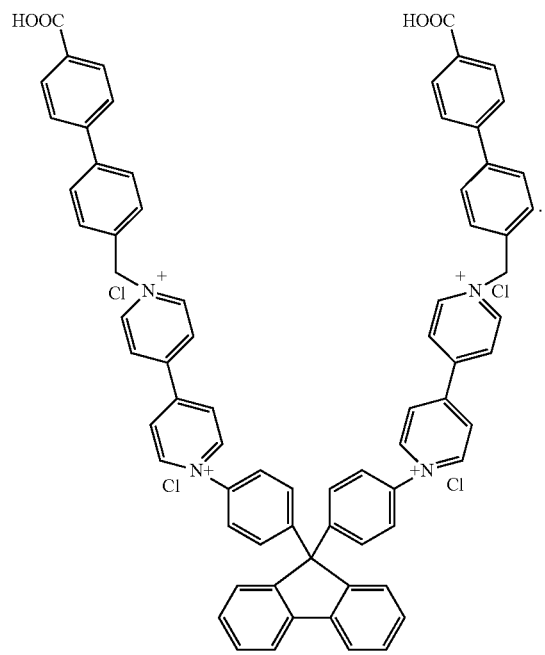

In the Chemical Formulas 1 to 3, $Z_1$ to $Z_3$ may each independently be represented by Chemical Formula B:

$$-R_{14}-Y-R_{15}-$$ Chemical Formula B wherein Y is a $C_2$ to $C_{20}$ heteroarylene group, which includes at least one nitrogen, and $R_{14}$ and $R_{15}$ are each independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

Y may be selected from the radicals represented by Chemical Formula C:

Chemical Formula C

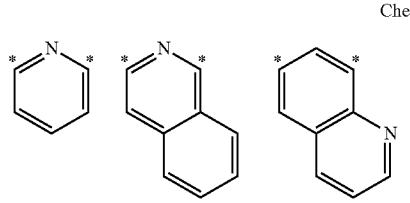

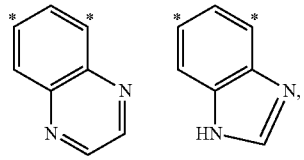

in which * represents a point of attachment.

The compound may express a dark blue color or a violet color.

The electrochromic material may include a compound represented by Chemical Formula 3F:

Chemical Formula 3F

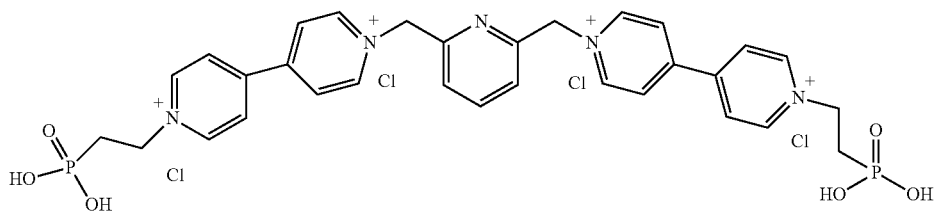

The electrochromic material may include a first compound expressing a green color and a second compound expressing a dark blue color or a violet color, the first compound may be a compound of Chemical Formulas 1 to 3, wherein $Z_1$ to $Z_3$ are each independently selected from the radicals of Chemical Formula A:

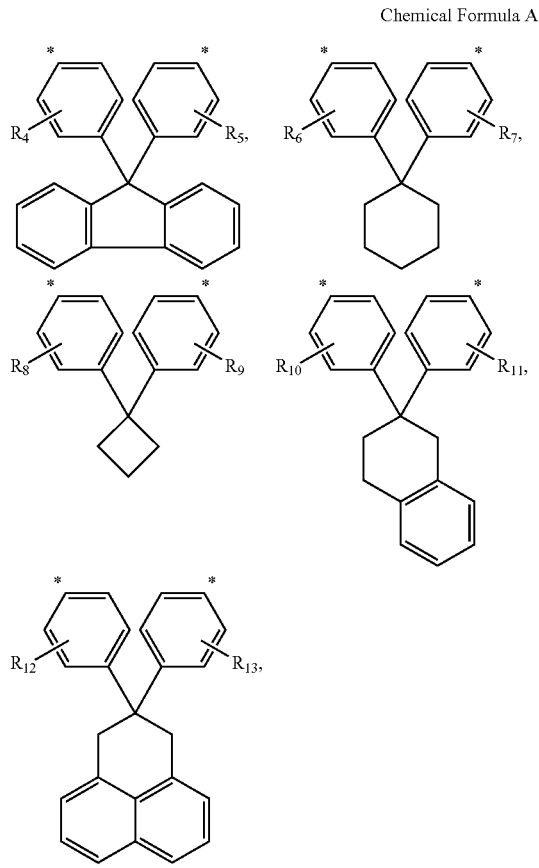

Chemical Formula A wherein $R_4$ to $R_{13}$ are independently selected from hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group, a halogen group, a halogen-containing group or a combination thereof, and the second compound may be a compound of Chemical Formulas 1 to 3, wherein $Z_1$ to $Z_3$ are each independently represented by Chemical Formula B:

$$—R_{14}—Y—R_{15}—, \qquad \text{Chemical Formula B}$$

wherein Y is a $C_2$ to $C_{20}$ heteroarylene group, which includes at least one nitrogen, and $R_{14}$ and $R_{15}$ are independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

The electrochromic material may further include an electrochromic compound expressing a red color. The electrochromic device may have an operating voltage of equal to or greater than about 0.9 volts.

The electrochromic device may have a potential window of about 0.9 volts to about 1.8 volts.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other aspects, advantages and features of this disclosure will become more apparent by describing in further detail exemplary embodiments thereof with reference to the accompanying drawings, in which.

DETAILED DESCRIPTION

Figure 1:
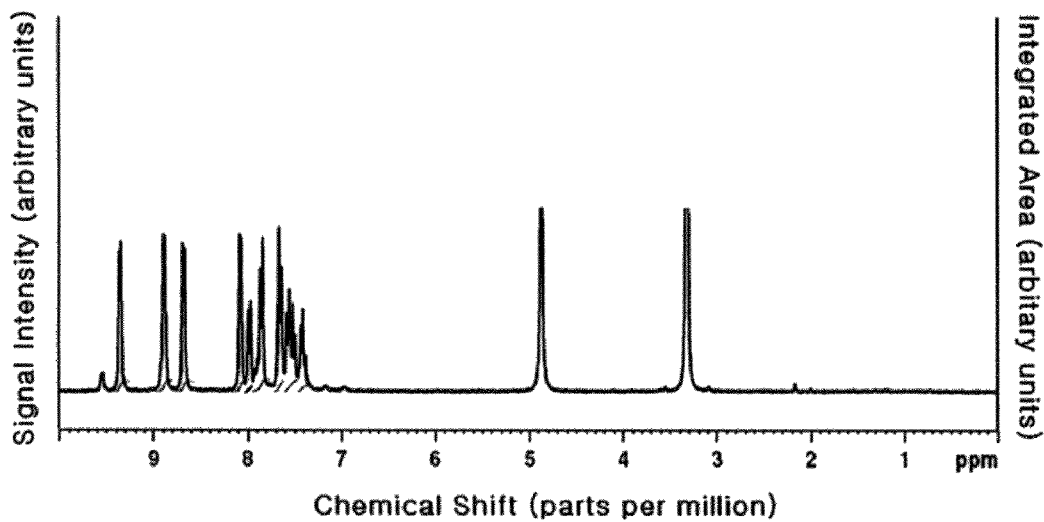
FIGS. 1 to 8 are $^1$H NMR spectra illustrating intensity (arbitrary units) and integrated area (arbitrary units) versus chemical shift (parts per million) of exemplary embodiments of the electrochromic compounds according to Examples 1, 2, 3, 7, 9, 10, 11 and 12, respectively.

Exemplary embodiments will be described more fully hereinafter with reference to the accompanying drawings. This disclosure may, however, be embodied in many different forms and should not be construed as limited to the exemplary embodiments set forth herein. Rather, these embodiments are provided so that this disclosure will be thorough and complete, and will fully convey the scope of the invention to those skilled in the art.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present disclosure.

The terminology used herein is for the purpose of describing particular embodiments only and is not intended to be limiting. As used herein, the terms "a" and "an" are open terms that may be used in conjunction with singular items or with plural items, and thus the singular forms are intended to include the plural forms as well, unless the context clearly states otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs.

As used herein, unless otherwise provided, the term "substituted" refers to a compound or radical substituted with at least one (e.g., 1, 2, 3, 4, 5, 6 or more) substituents independently selected from a halogen (e.g., F, Cl, Br, I), a hydroxyl, an alkoxy, a nitro, a cyano, an amino, an azido, an amidino, a hydrazino, a hydrazono, a carbonyl, a carbamyl, a thiol, an ester, a carboxyl, or a salt thereof, sulfonic acid or a salt thereof, phosphoric acid or a salt thereof, a $C_1$ to $C_{20}$ alkyl, a $C_2$ to $C_{16}$ alkynyl, a $C_6$ to $C_{20}$ aryl, a $C_7$ to $C_{13}$ arylalkyl, a $C_1$ to $C_4$ oxyalkyl, a $C_1$ to $C_{20}$ heteroalkyl, a $C_3$ to $C_{20}$ heteroaryl (i.e., a group that comprises at least one aromatic ring, wherein at least one ring member is other than carbon), a $C_3$ to $C_{20}$ heteroarylalkyl, a $C_3$ to $C_{20}$ cycloalkyl, a $C_3$ to $C_{15}$ cycloalkenyl, a $C_6$ to $C_{15}$ cycloalkynyl, a $C_5$ to $C_{15}$ heterocycloalkyl or a combination thereof, instead of hydrogen, provided that the substituted atom's normal valence is not exceeded.

It is to be understood that in the structures drawn herein, "X" and "Cl" have a negative charge where chemically required to balance the positive charge shown.

Hereinafter, the electrochromic material according to an embodiment is described.

The electrochromic material may comprise a single electrochromic compound or may comprise a mixture of electrochromic compounds.

The electrochromic material according to one embodiment includes at least one compound represented by the following Chemical Formulas 1 to 3.

Chemical Formula 1

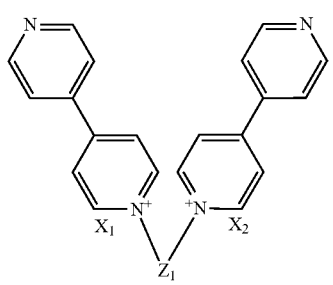

Chemical Formula 2

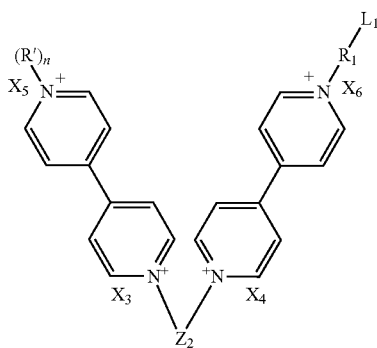

Chemical Formula 3

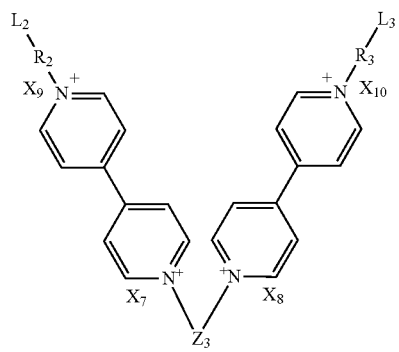

In Chemical Formulas 1 to 3, $Z_1$ to $Z_3$ are each independently selected from a substituted or unsubstituted $C_6$ to $C_{30}$ arylene group, a substituted or unsubstituted $C_2$ to $C_{30}$ heteroarylene group, a substituted or unsubstituted $C_3$ to $C_{30}$ cycloalkylene group or a combination thereof. As used herein, the term "arylene" refers to a bivalent radical formed by the removal of two hydrogen atoms from one or more rings of an aromatic hydrocarbon, wherein the hydrogen atoms may be removed from the same or different rings (preferably different rings), each of which rings may be aromatic or nonaromatic. "Heteroarylene" refers to a bivalent radical formed by the removal of two hydrogen atoms from one or more rings of heteroaryl moiety, wherein the hydrogen atoms may be removed from the same or different rings (preferably the same ring), each of which rings may be aromatic or nonaromatic. "Cycloalkylene" refers to a bivalent radical formed by the removal of two hydrogen atoms from one or more rings of a cycloalkyl group (a nonaromatic hydrocarbon that comprises at least one ring).

$R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof.

R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof. In Chemical Formula 2 n is 0 or 1.

$L_1$ to $L_3$ are each independently selected from a phosphonic acid group, a carboxylic acid group, a sulfonic acid group and a hydroxyl group or a combination thereof.

$X_1$ to $X_{10}$ are each independently a halogen group, a halogen-containing group or a combination thereof and may be, for example, $Br^-$, $Cl^-$, $BF_4^-$, $PF_6^-$, $ClO_4^-$, $CF_3SO_3^-$ or a combination thereof.

The electrochromic material according to an embodiment may comprise at least one compound represented by the Chemical Formulas 1 to 3, wherein $Z_1$ to $Z_3$ are each independently selected from a radical of Chemical Formula A. The compound represented by Chemical Formulas 1 to 3 may be electrochromic, thus may be an electrochromic compound, and may be referred to as an electrochromic compound. The compound represented by Chemical Formulas 1 to 3 may be colored, and may be green, thus may express green.

Chemical Formula A

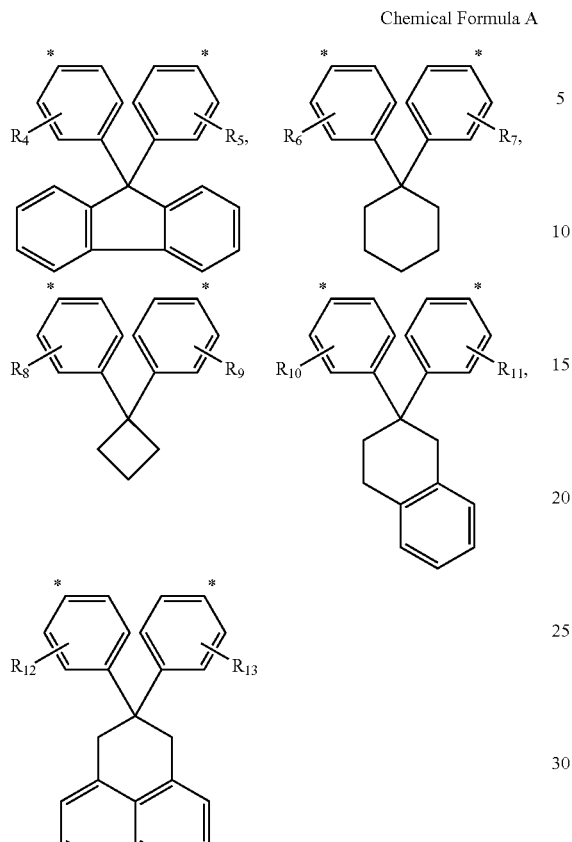

Herein, "*" denotes a bonding position, e.g., a point of attachment.

In the Chemical Formula A, $R_4$ to $R_{13}$ are each independently selected from hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group, a halogen group, a halogen-containing group or a combination thereof.

As an electrochromic compound expressing green, the compound of the Chemical Formula 1 may include a compound represented by Chemical Formulas 1A to 1C.

Chemical Formula 1A

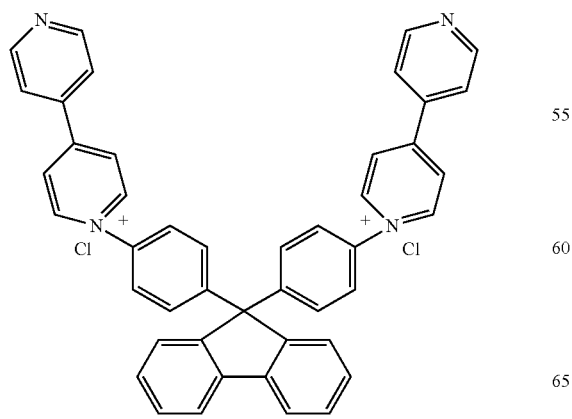

Chemical Formula 1B

Chemical Formula 1C

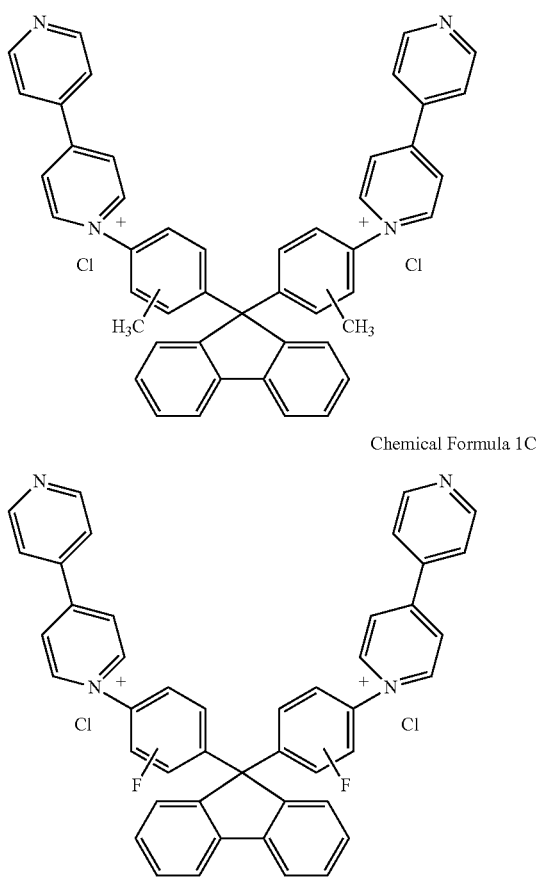

The compound represented by the Chemical Formula 2, which may be electrochromic, may include at least one compound of Chemical Formulas 2A to 2C.

Chemical Formula 2A

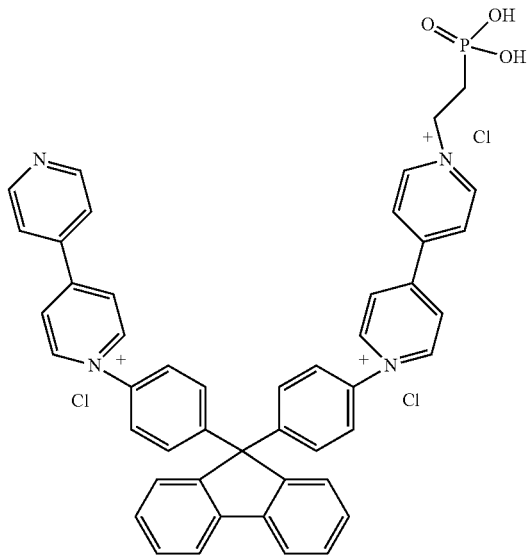

Chemical Formula 2B
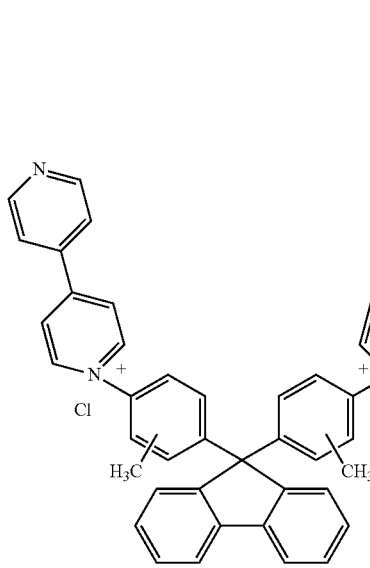
Chemical Formula 2C
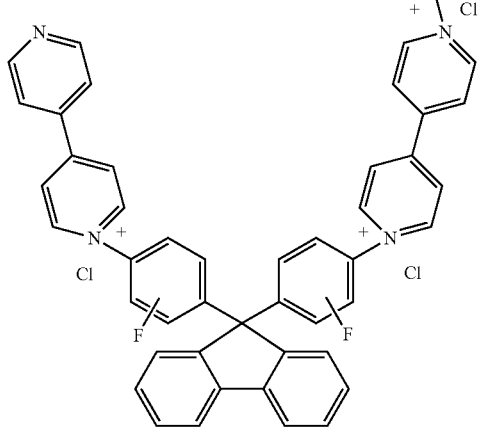
Chemical Formula 3A
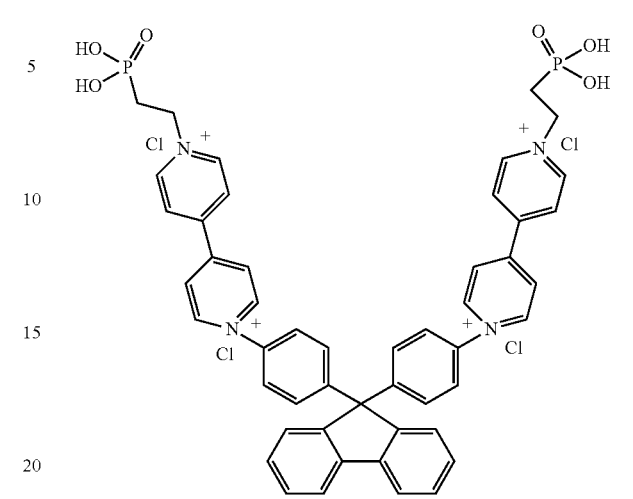
Chemical Formula 3B
Chemical Formula 3C
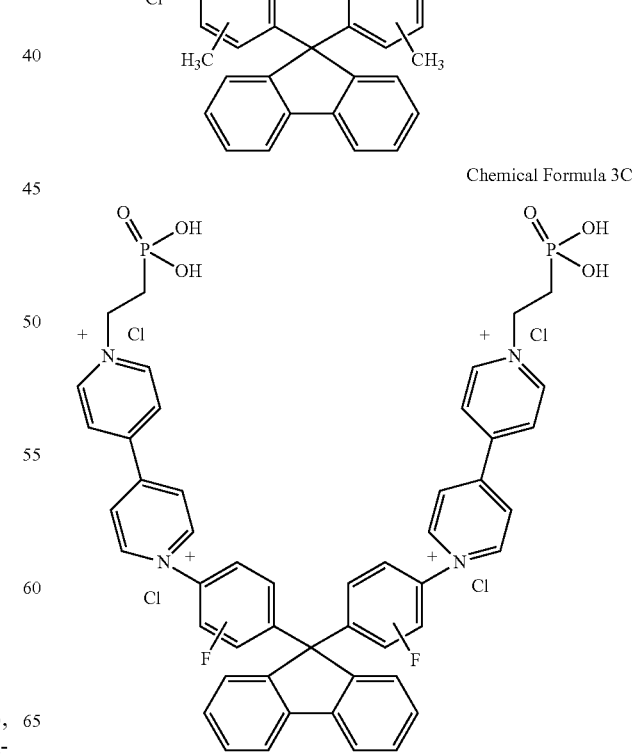
The compound represented by the Chemical Formula 3, which may be electrochromic, may include at least one compound of Chemical Formulas 3A to 3E.

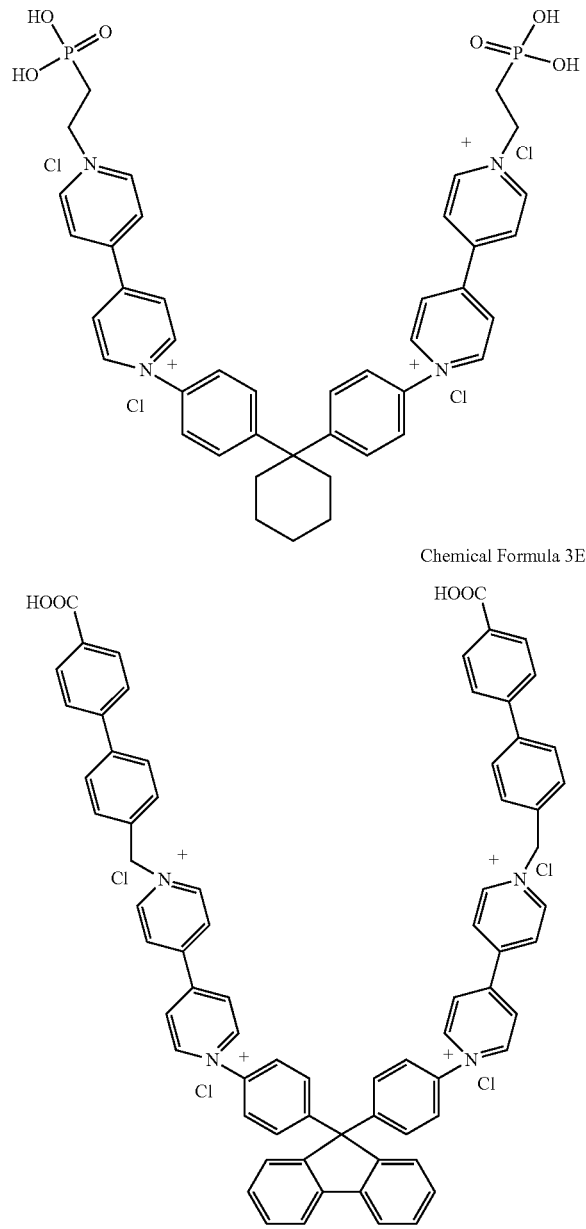

Chemical Formula 3D

Chemical Formula 3E

In Chemical Formulas 1 to 3, in an embodiment, the compound includes two viologens and linkers $Z_1$, $Z_2$ and $Z_3$ positioned between the two viologens.

The viologens are 4,4'-bipyridyl derivatives that reversibly change color by oxidation and reduction. For example, the viologen may be colorless in an oxidized state, and may express a color (e.g., be colored) in a reduced state.

The linkers $Z_1$, $Z_2$ and $Z_3$ are positioned between the two viologens and are believed to control an extent of oxidation and reduction by controlling electron mobility.

The linkers $Z_1$, $Z_2$ and $Z_3$ include discontinuously positioned arylene groups, as in Chemical Formula A. The discontinuously positioned arylene groups are believed to induce discontinuous pi-conjugation, and thus control electron transfer to a viologen.

The linkers $Z_1$, $Z_2$ and $Z_3$ positioned between two viologens may show a steric hindrance effect due to their bulkiness. Thereby, the stacking effect, whereby two viologens are positioned closer to each other in one compound or viologens of adjacent compounds interact with each other, may be inhibited.

The extent of oxidation and reduction of viologens may be controlled by the structure of a compound, resulting in an increase in operating voltage. The operating voltage refers to a voltage sufficient to reduce an electrochromic material, thereby expressing a color, or a voltage sufficient to oxidize an electrochromic material, thereby rendering it substantially colorless.

The compounds represented by the Chemical Formulas 2 and 3 include terminal groups $L_1$, $L_2$ or $L_3$ at the terminal ends of at least one viologen. The terminal groups may improve the memory effect. The memory effect refers to maintenance of the same color within a selected voltage range.

The following Reaction Scheme 1 shows oxidation and reduction of an electrochromic compound represented by the Chemical Formula 3C wherein the linker $Z_3$ is 9,9-diphenylfluorene.

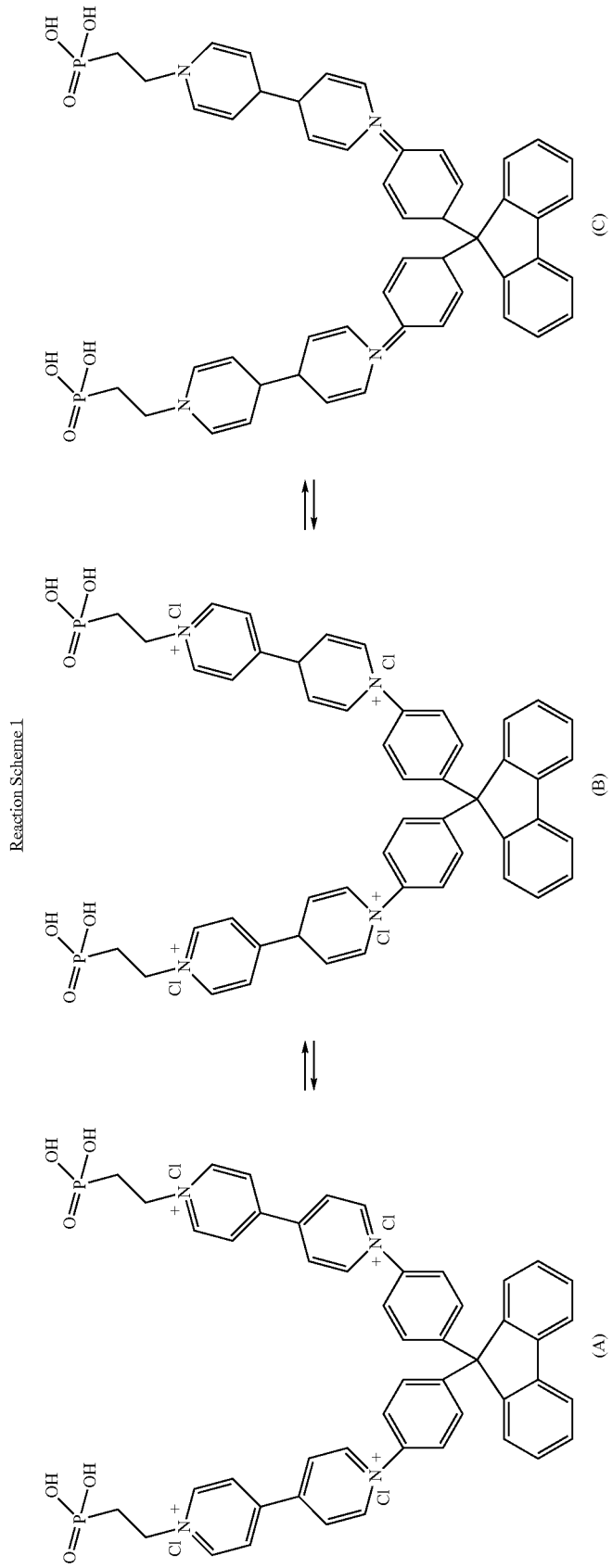
Reaction Scheme 1

In the Reaction Scheme 1, state (A) is an oxidation state that is substantially colorless, state (B) is a first reduced state expressing a color, and state (C) shows a second reduced state also expressing a color. State (A) does not express a color and states (B) and (C) express a green color. In order for the compound of Chemical Formula 3C be reduced from state (A) to state (B), an operating voltage ("E1") is required.

As disclosed above, the electrochromic compound according to an embodiment has a novel structure and has a high operating voltage ("E1"), for example equal to or greater than about 0.5 volts (V), specifically equal to or greater than about 0.9 V, more specifically equal to or greater than about 1 V. The electrochromic compound according to an embodiment has a wide potential window of about 0.5 to about 4 V, specifically about 0.9 to about 1.8V, more specifically about 1 to about 1.5 V. The potential window refers to a voltage range in which a color is maintained.

In the electrochromic compound represented by the Chemical Formulas 1 to 3, $Z_1$ to $Z_3$ are each independently represented by Chemical Formula B. In this embodiment, the compound may be electrochromic and express a dark blue color or a violet color.

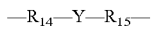

Chemical Formula B

In the Chemical Formula B, Y is a $C_2$ to $C_{20}$ heteroarylene group, which includes at least one nitrogen, and $R_{14}$ and $R_{15}$ are each independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

Y may be selected from the group of radicals represented by Chemical Formula C.

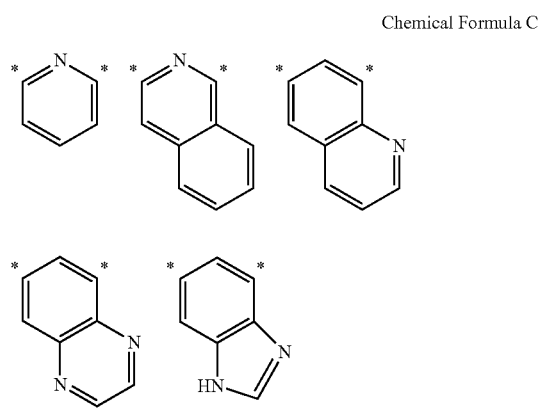

Chemical Formula C

Herein, "*" denotes a bonding position, e.g., a point of attachment.

The electrochromic compound expressing dark blue color or a violet color may be represented by Chemical Formula 3F.

The electrochromic compound has a high operating voltage, and may further include another color expressing moiety, which is colored within the operating voltage therein. For example, the electrochromic compound may include a red-expressing moiety and a blue-expressing moiety, which are colored at about 1 V, resulting in expression of a dark blue color or a violet color.

In another embodiment, electrochromic compounds expressing different colors may be mixed, thus the electrochromic material may comprise a mixture of electrochromic compounds. For example, the green-expressing electrochromic compound and the dark blue color or violet color-expressing electrochromic compound may be mixed to express deep violet color.

A red electrochromic compound may be mixed with the green-expressing electrochromic compound and the dark blue color or violet color-expressing electrochromic compound resulting in expression of black. As the red electrochromic compound, any red-expressing electrochromic compound may be used without limitation.

Hereinafter, an electrochromic device using the electrochromic material is described referring to FIG. 28.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for Chemical Formula 3F

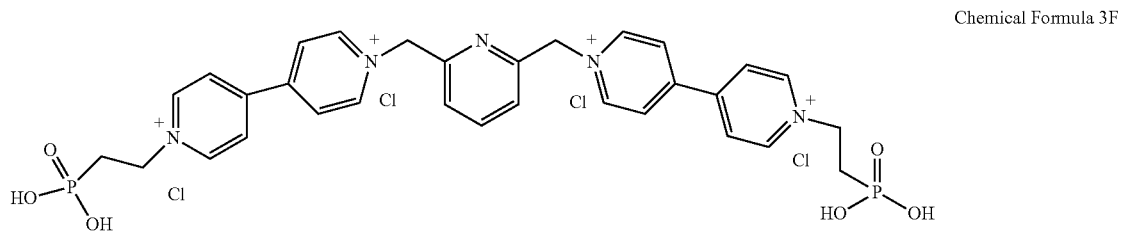

example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

Figure 28:
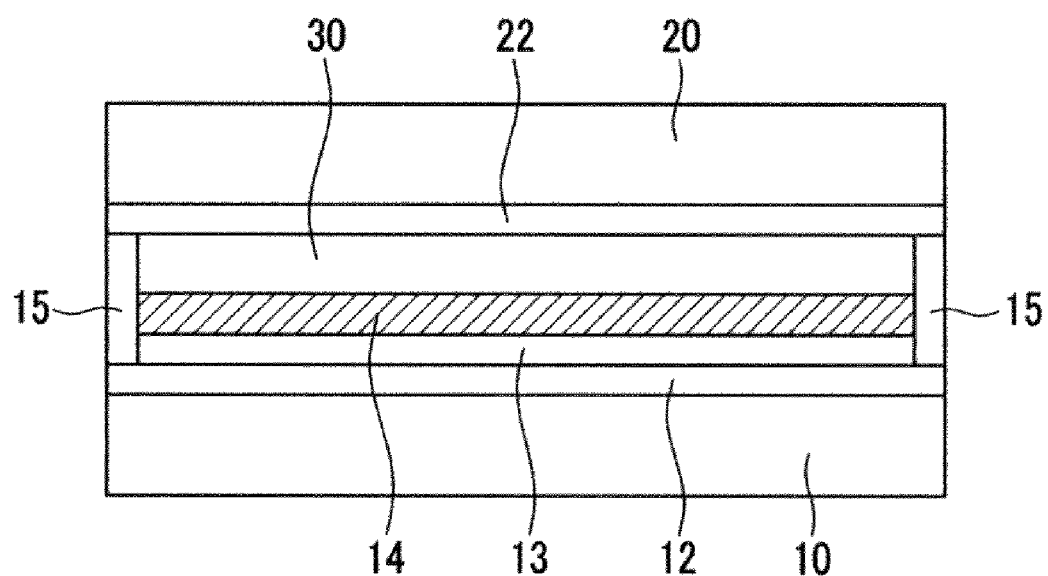
FIG. 28 is a schematic cross-sectional view of an exemplary embodiment of an electrochromic device.

FIG. 28 is a schematic cross-sectional view of an electrochromic device according to an embodiment.

Referring to FIG. 28, the electrochromic device according to an embodiment includes first and second insulating substrates 10 and 20 facing each other, and a first electrode 12 and a second electrode 22 disposed on the first and second insulating substrates 10 and 20, respectively.

The first and second insulating substrates 10 and 20 may comprise transparent glass, plastic or the like or a combination thereof. Examples of the plastic include one or more selected from polyacrylate, polyethylene etherphthalate, polyethylene naphthalate, polycarbonate, polyarylate, polyetherimide, polyethersulfone and polyimide.

The first electrode 12 includes a transparent conductive material, for example to an inorganic conductive material including indium tin oxide ("ITO") or fluorine-doped tin oxide ("FTO"), or an organic conductive material, such as polyacetylene, polythiophene or the like.

The second electrode 22 may comprise a transparent or opaque conductive material, for example indium tin oxide ("ITO"), fluorine-doped tin oxide ("FTO"), a metal, such as Al, antimony-doped tin oxide ("ATO") or a combination thereof.

An electrochromic layer 14 including the electrochromic material is disposed on the first electrode 12. An auxiliary layer 13 may be disposed between the first electrode 12 and the electrochromic layer 14 and may improve adherence of the electrochromic layer 14. The auxiliary layer 13 may include titanium oxide (e.g., $TiO_2$) and the like, and may be omitted.

A reflector (not shown) may be disposed under the second electrode 22.

The first insulating substrate 10 and the second insulating substrate 20 are fixed by spacers 15, and an electrolyte 30 is disposed between the first insulating substrate 10 and the second insulating substrate 20. The electrolyte 30 includes an oxidation/reduction material, which oxidizes and reduces the electrochromic material, and the electrolyte may be a liquid electrolyte or a solid polymer electrolyte. The liquid electrolyte may include a solution wherein a lithium salt, such as LiOH or $LiClO_4$, a potassium salt, such as KOH, a sodium salt, such as NaOH, or the like, is dissolved in a solvent, but is not limited thereto. The solid electrolyte may include poly(2-acrylamino-2-methylpropane sulfonic acid), polyethylene oxide, or the like, but is not limited thereto.

The following examples illustrate this disclosure in more detail. However, it is understood that this disclosure is not limited by these examples.

Example 1

Synthesis of a Compound of Chemical Formula 1A

A 0.348 gram (g) (1 millimole, mmol) amount of 9,9-(4-aminophenyl)fluorene and 0.716 g (2 mmol) of 4-(2,4-dinitrophenyl)-4,4'-dipyridyl are refluxed in 200 milliliters (mL) of ethanol for 7 days. The solvent is evaporated and the resultant yellow solid is dissolved in a minimum quantity of methanol followed by the addition of acetone until precipitation. The precipitate is filtered, washed several times with acetone, and dried in an oven at 70° C. to obtain a compound of Chemical Formula 1A, as shown in Chemical Reaction Scheme 1.

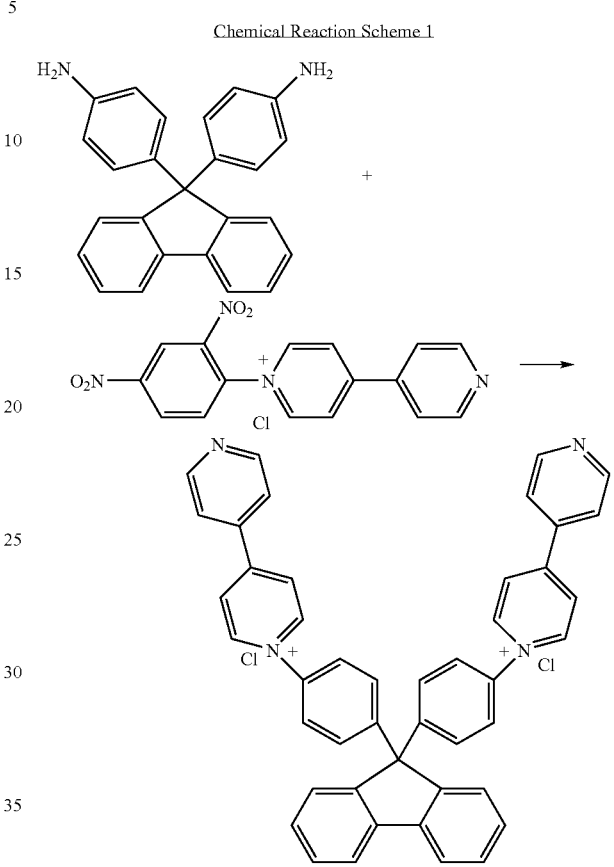

Chemical Reaction Scheme 1

The molecular structure of the compound prepared according to Example 1 is confirmed by the $^1H$ NMR spectrum shown in FIG. 1.

Fabrication of Electrochromic Device and Measurement of Electrical Characteristics The obtained electrochromic material of Example 1 and 0.05 mmol of $LiClO_4$ as an electrolyte are dissolved in butyroacetone to obtain an electrochromic solution. Next, ITO electrodes are provided on each of two glass substrates, and titanium oxide ($TiO_2$) is coated thereon. The glass substrates are sealed using a spacer, and the electrochromic solution is injected between the glass substrates to fabricate a test cell.

A voltage of 0 V to 2.2 V is applied to the test cell to measure electrochromism.

Figure 16:
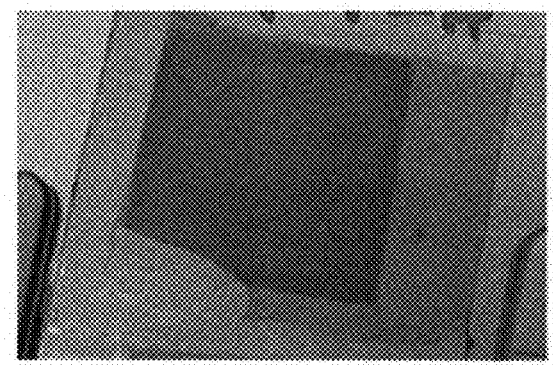
FIGS. 16 to 27 are photographs showing electrochromism of exemplary embodiments of the electrochromic device including the electrochromic materials according to Examples 1, 2, 3, 4, 7, 8, 9, 10, 11, 12, 13 and 14, respectively.

FIG. 16 shows that the test cell (electrochromic device) according to the present example expresses green. The electrochromic device has an operating voltage ("x") of about 0.9 V ($0.9 \leq x \leq 1.1$), and a potential window of about 0.9 to about 1.6 V. The operating voltage refers to a voltage needed to start electrochromism, and the potential window refers to a voltage range to maintain the color.

Example 2

Synthesis of a Compound of Chemical Formula 1B

A compound represented by Chemical Formula 1B, wherein a methyl group (—$CH_3$) is bonded to fluorene at a meta (m) position, is obtained according to the same method as in Example 1, except that 9,9-(4-amino-3-methylphenyl)fluorene is used instead of 9,9-(4-aminophenyl)fluorene), as further show in Chemical Reaction Scheme 2.

Chemical Reaction Scheme 2

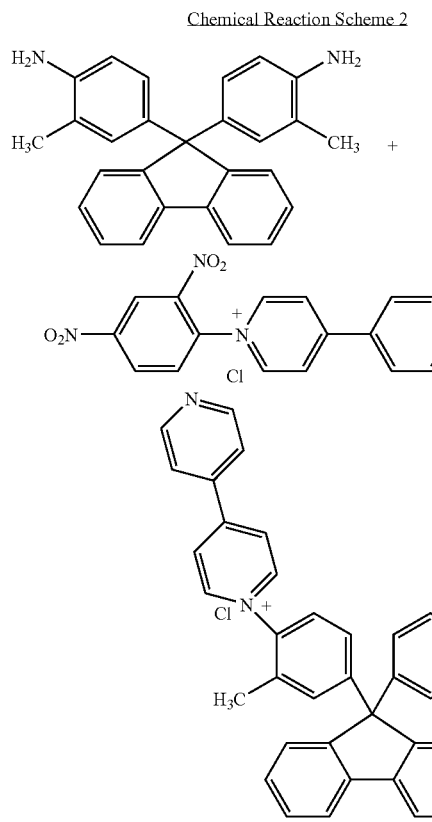

Figure 2:
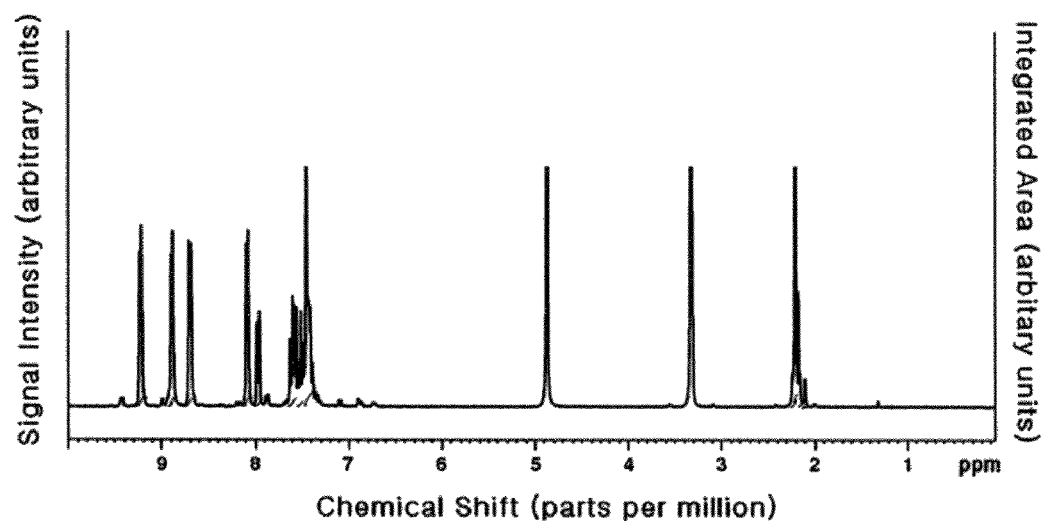

The molecular structure of the compound is confirmed by the $^1$H NMR spectrum shown in FIG. 2.

Fabrication of Electrochromic Device and Measurement of Electrical Characteristics The electrochromic device is fabricated according to the same method as in Example 1, except that the compound prepared in Example 2 is used instead of the compound of Example 1, and the voltage is applied to the electrochromic device.

Figure 17:
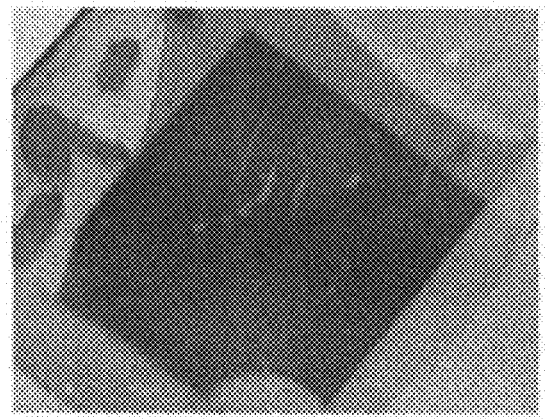

FIG. 17 shows that the electrochromic device according to the present example expresses bluish green light. The electrochromic device has an operating voltage ("x") of about 0.8 V ($0.8 \leq x \leq 1.1$), and a potential window of about 0.8 to about 1.5 V.

Example 3

Synthesis of a Compound of Chemical Formula 1C

A compound represented by Chemical Formula 1C wherein fluorine (F) is bonded to fluorene at a meta (m) position) is obtained according to the same method as in Example 1, except that 9,9-(4-amino-3-fluorophenyl)fluorene is used instead of 9,9-(4-aminophenyl)fluorene), as shown in Chemical Reaction Scheme 3.

Chemical Reaction Scheme 3

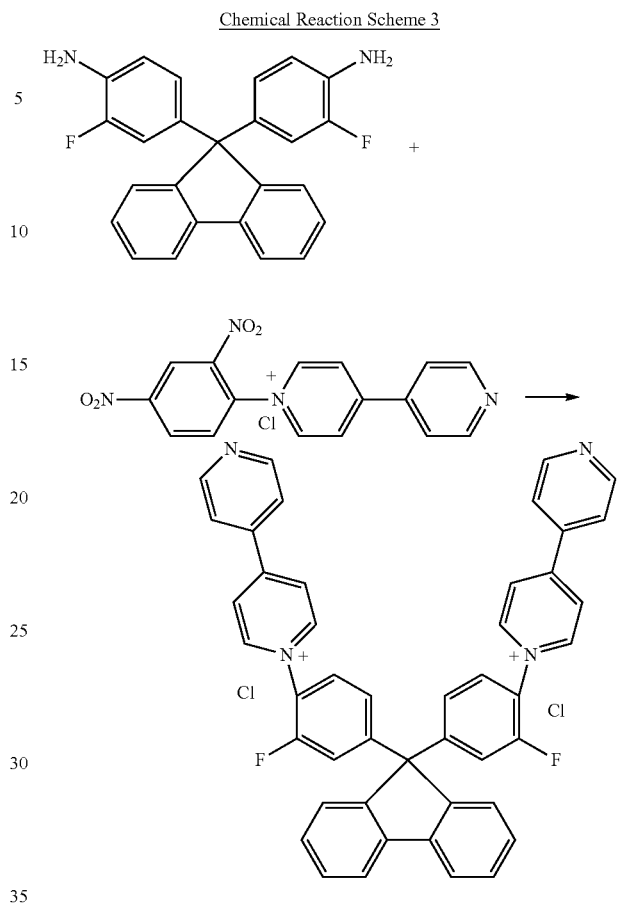

Figure 3:
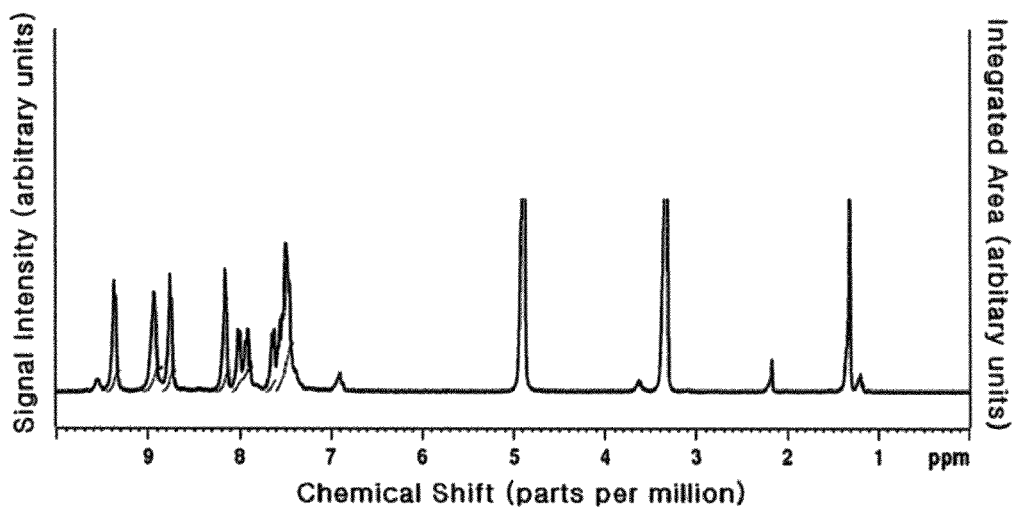

The molecular structure of the compound of Example 3 is confirmed by the $^1$H NMR spectrum shown in FIG. 3.

Fabrication of Electrochromic Device and Measurement of Electrical Characteristics The electrochromic device is fabricated according to the same method as in Example 1, except that the compound of Example 3 is used instead of the compound of Example 1, and the voltage is applied to the electrochromic device to measure electrochromism.

Figure 18:
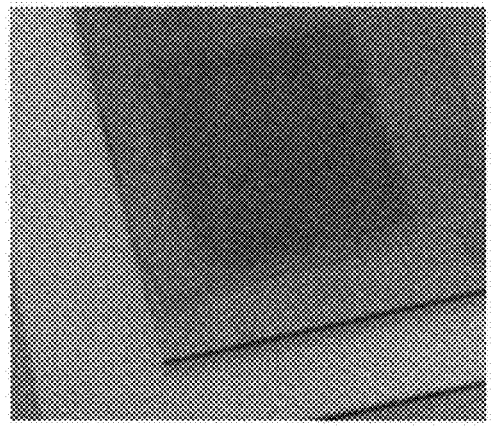

FIG. 18 shows that the electrochromic device according to the present example expresses bluish green. The electrochromic device has an operating voltage ("x") of about 0.9V ($0.9 \leq x \leq 1.1$), and a potential window of about 0.9 to about 1.6V.

Example 4

Synthesis of a Compound of Chemical Formula 2A

To 0.699 g (1 mmol) of the compound of Example 1 in 30 mL of refluxing acetonitrile, 2.45 g (10 mmol) of the compound diethyl 2-bromoethylphosphonate is added and refluxed for 7 days. The solvent is evaporated under reduced pressure to obtain a yellow-brown solid. The yellow-brown solid is treated with hot acetonitrile and filtered, followed by precipitation with a solution of methanol and acetone to obtain a brownish yellow solid, as shown in Chemical Reaction Scheme 4.

Chemical Reaction Scheme 4

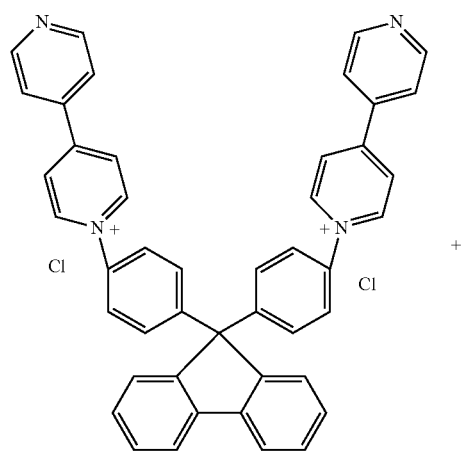

+

Chemical Reaction Scheme 5

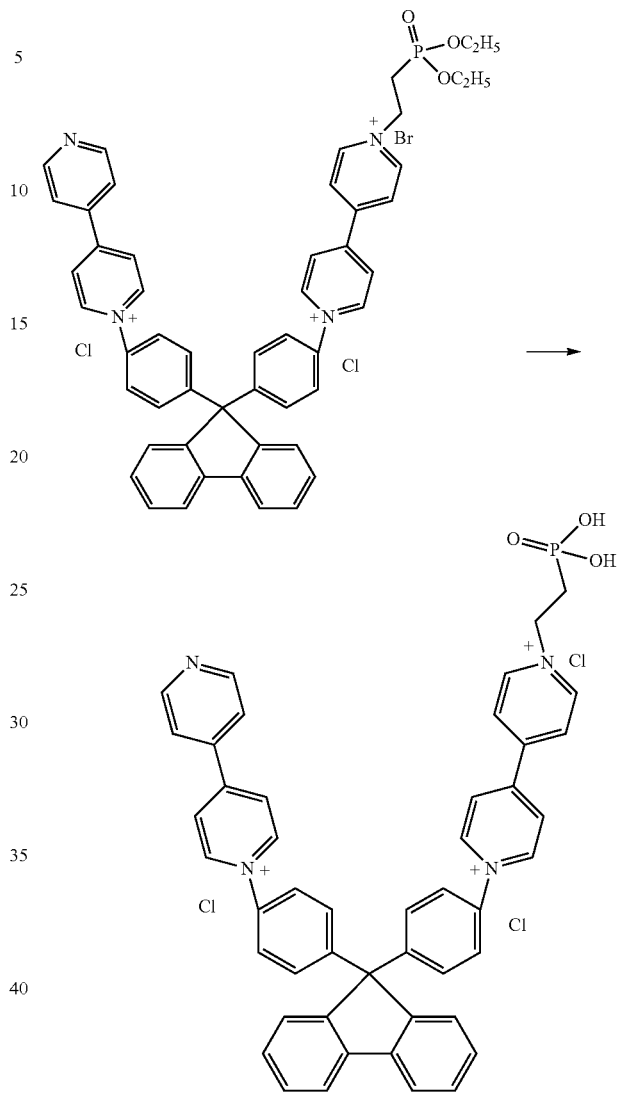

The brownish yellow solid is then refluxed in 80 mL of 35% hydrochloric acid for one day. The yellow colored residue is filtered and is dissolved in methanol. Next, the resulting precipitate is filtered to obtain the compound of Chemical Formula 2A as shown in Chemical Reaction Scheme 5.

The molecular structure of the compound is confirmed by $^1$H NMR spectroscopy. It is confirmed that a phosphonic acid group is only attached to one pyridyl (viologen) moiety.

Fabrication of Electrochromic Device and Measurement of Electrical Characteristics The electrochromic device is fabricated according to the same method as in Example 1, except that the compound of Example 4 used instead of the compound of Example 1, and the voltage is applied to the electrochromic device to measure electrochromism.

Figure 19:
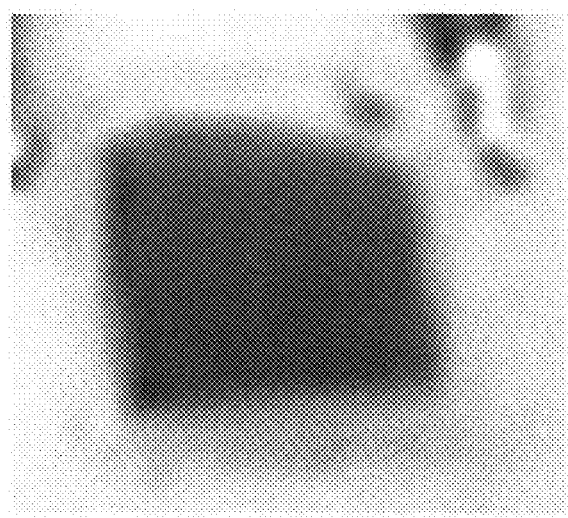

FIG. 19 shows that the electrochromic device according to the present example expresses green. The electrochromic device shows an operating voltage ("x") of about 0.9V $(0.9 \leq x \leq 1.1)$, and a potential window of about 0.9 to about 1.5 V.

Example 5

Synthesis of a Compound of Chemical Formula 2B

A compound represented by Chemical Formula 2B wherein a methyl group (—CH$_3$) is bonded to fluorene at a meta (m) position is obtained according to the same method as in Example 4, except that the compound of Example 2 is used instead of the compound of Example 1.

Fabrication of Electrochromic Device and Measurement of Electrical Characteristics The electrochromic device is fabricated according to the same method as in Example 1, except that the compound of Example 5 is used instead of the compound of Example 1, and the voltage is applied to the electrochromic device to measure electrochromism.

The electrochromic device shows green electrochromism at an operating voltage ("x") of about 0.9 V ($0.9 \leq x \leq 1.1$), and maintains the same color up to about 1.6 V.

Example 6

Synthesis of a Compound of Chemical Formula 2C

A compound represented by Chemical Formula 2C wherein fluorine (F) is bonded to fluorene at a meta (m) position) is obtained according to the same method as in Example 4, except that the compound of Example 3 is used instead of the compound of Example 1.

Fabrication of Electrochromic Device and Measurement of Electrical Characteristics The electrochromic device is fabricated according to the same method as in Example 1, except that the compound of Example 6 is used instead of the compound of Example 1, and the voltage is applied to the electrochromic device to measure electrochromism.

The electrochromic device shows green electrochromism at an operating voltage ("x") of about 0.8V ($0.8 \leq x \leq 1.1$), and maintains the same color up to about 2.1V.

Example 7

Synthesis of a Compound of Chemical Formula 3A

A 0.348 g (1 mmol) amount of 9,9-(4-aminophenyl)fluorene and 1.206 g (2 mmol) of 4-(2,4-dinitrophenyl)-4'-(ethyldiethyl phosphonate)-4,4'-dipyridyl are refluxed in 200 mL of ethanol for 7 days. The solvent is removed to obtain a yellow solid. The yellow solid is dissolved in a minimum quantity of methanol followed by the addition of acetone until precipitation. The precipitate is filtered, washed several times with acetone, and dried in an oven at 70° C. This portion of the synthesis is shown in Chemical Reaction Scheme 6.

Chemical Reaction Scheme 6

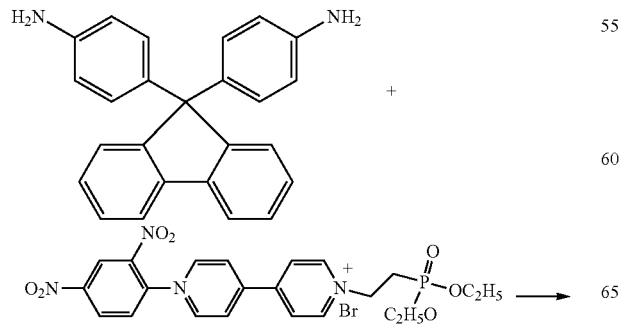

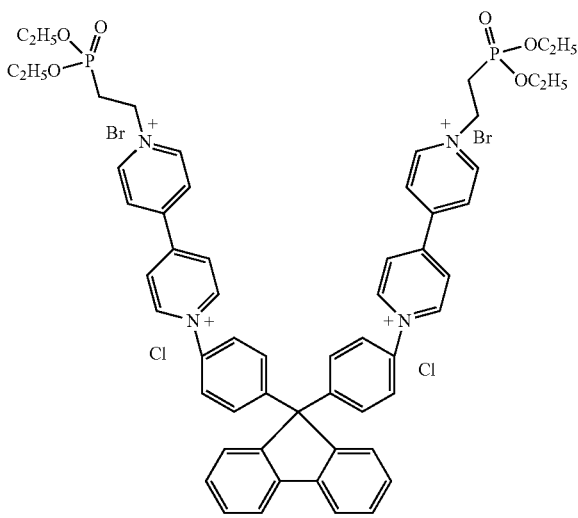

The solid is then refluxed in 80 mL of 35% hydrochloric acid for one day. The yellow colored residue is filtered and is dissolved in methanol. Next, the resulting precipitate is filtered to obtain the compound of Chemical Formula 3A as shown in Chemical Reaction Scheme 7.

Chemical Reaction Scheme 7

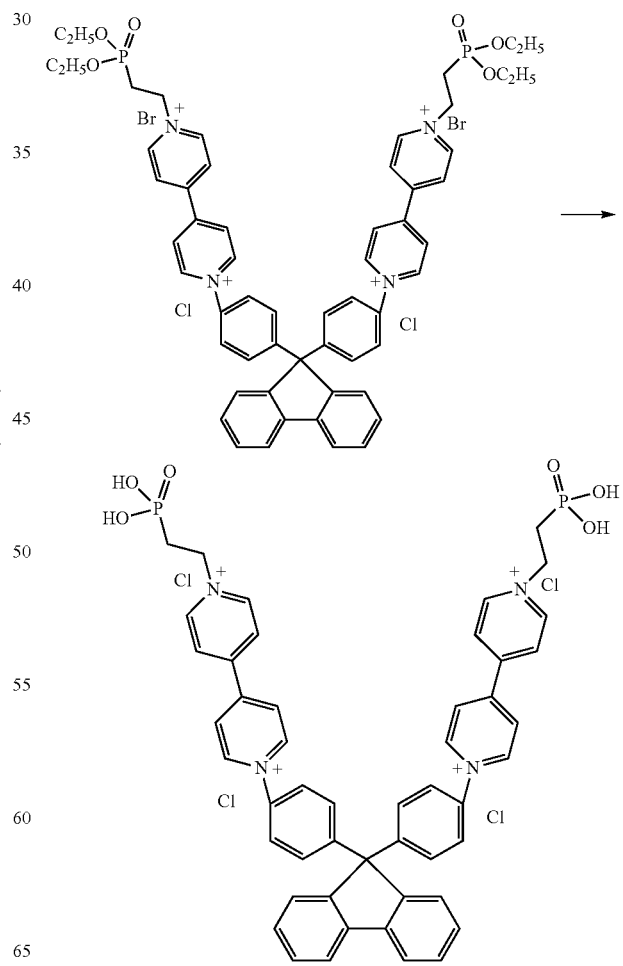

Figure 4:
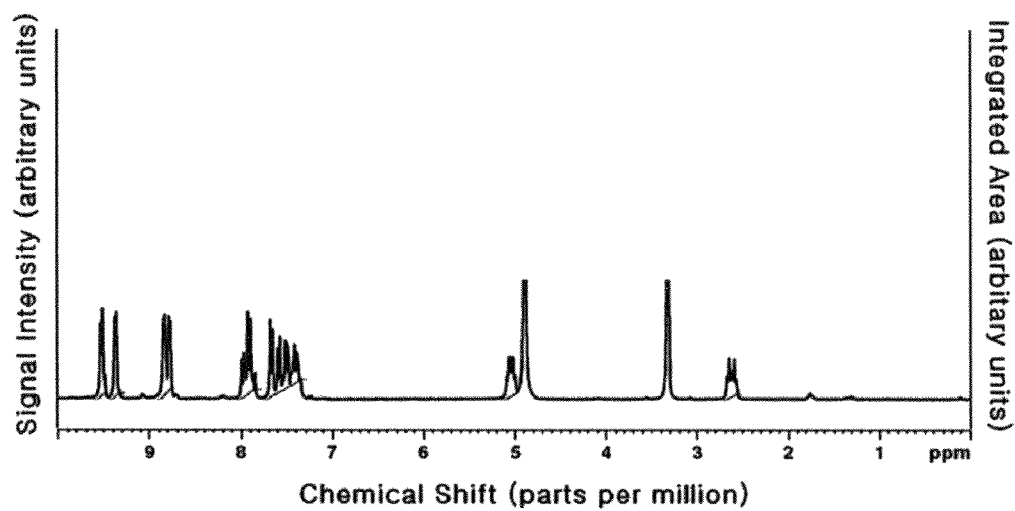

The molecular structure of the compound is confirmed by the $^1$H NMR spectrum shown in FIG. 4. It is confirmed that a phosphonic acid group is attached to two pyridyl (viologen) moieties.

Fabrication of Electrochromic Device and Measurement of Electrical Characteristics The electrochromic device is fabricated according to the same method as in Example 1, except that the compound prepared in Example 7 is used instead of the compound of Example 1, and the voltage is applied to the electrochromic device to measure electrochromism.

Figure 20:
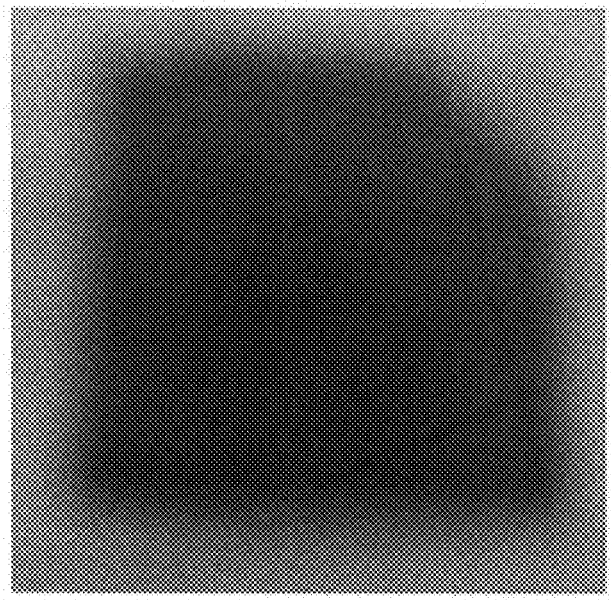

FIG. 20 shows that the electrochromic device according to the present example expresses green. The electrochromic device shows an operating voltage ("x") of about 0.9 V ($0.9 \leq x \leq 1.1$), and a potential window of about 0.9 to about 1.8 V.

Example 8

Synthesis of a Compound of Chemical Formula 3B

A compound represented by Chemical Formula 3B wherein a methyl group (—CH$_3$) is bonded to fluorene at a meta (m) position) is obtained according to the same method as in Example 7, except that 9,9-(4-amino-3-methylphenyl) fluorene is used instead of 9,9-(4-aminophenyl)fluorene, as shown in Chemical Reaction Schemes 8 and 9.

Chemical Reaction Scheme 8

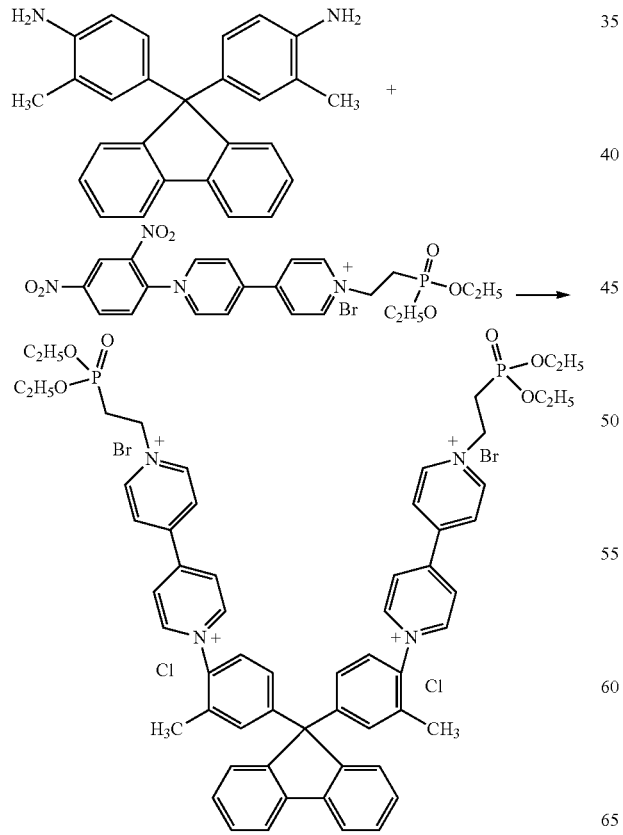

Chemical Reaction Scheme 9

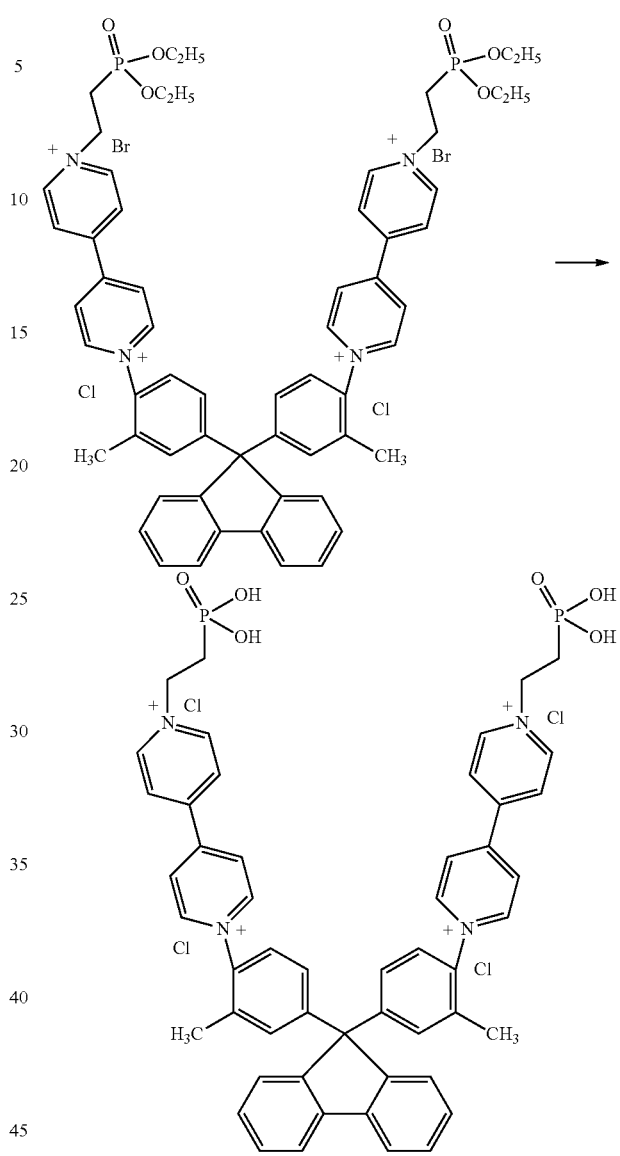

Figure 5:
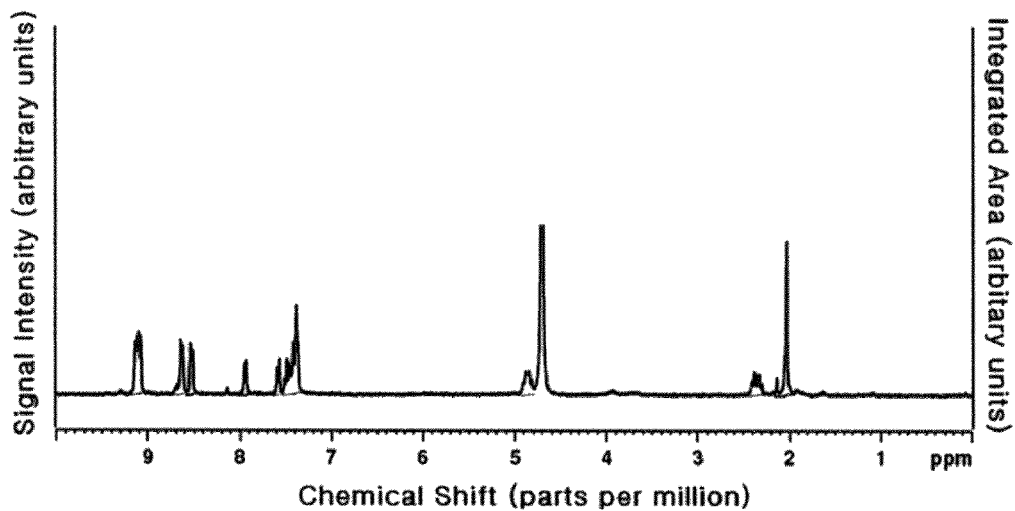

The molecular structure of the compound is confirmed by the $^1$H NMR spectrum shown in FIG. 5. It is confirmed that a phosphonic acid group is attached to two pyridyl (viologen) moieties.

Fabrication of Electrochromic Device and Measurement of Electrical Characteristics The electrochromic device is fabricated according to the same method as in Example 1, except that the compound prepared in Example 8 is used instead of the compound of Example 1, and the voltage is applied to the electrochromic device excepting the electrochromic material to measure electrochromism.

Figure 21:
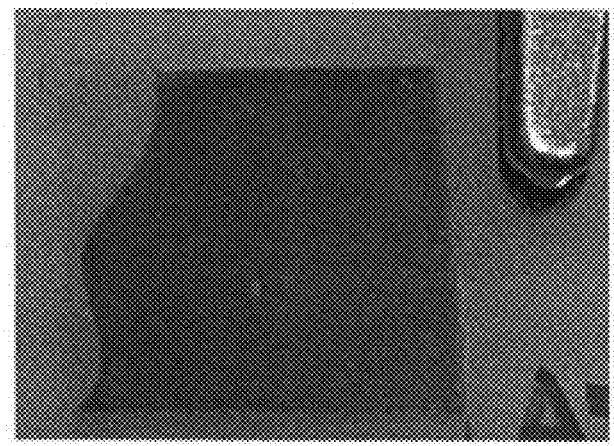

FIG. 21 shows that the electrochromic device according to the present example expresses bluish green. The electrochromic device shows an operating voltage ("x") of about 0.9 V ($0.9 \leq x \leq 1.1$), and a potential window of about 0.9 to about 1.5 V.

Example 9

Synthesis of a Compound of Chemical Formula 3C

A compound represented by Chemical Formula 3C wherein fluorine (F) is bound to fluorene at a meta (m) position) is obtained according to the same method as in Example 7, except that 9,9-(4-amino-3-fluorophenyl)fluorene is used instead of 9,9-(4-aminophenyl)fluorene.

Chemical Reaction Scheme 10

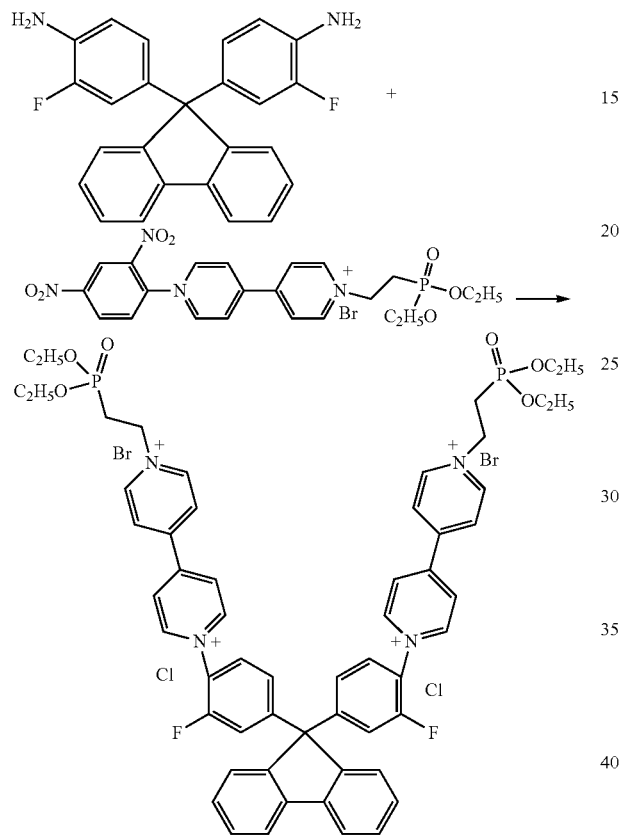

Chemical Reaction Scheme 11

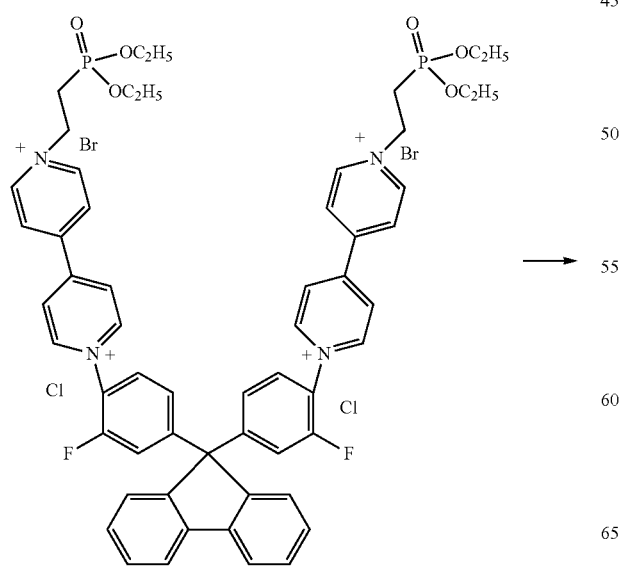

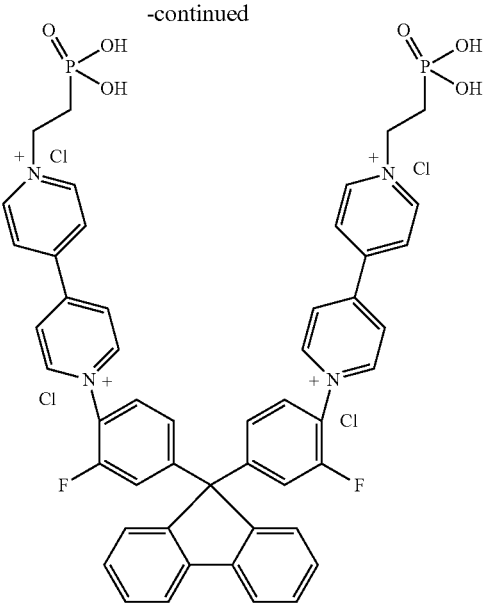

The molecular structure of the compound is confirmed by the $^1$H NMR spectrum shown in FIG. 5. It is confirmed that a phosphonic acid group is attached to two pyridyl (viologen) moieties.

Fabrication of Electrochromic Device and Measurement of Electrical Characteristics The electrochromic device is fabricated according to the same method as in Example 1, and the voltage is applied to the electrochromic device excepting the electrochromic material to measure electrochromism.

Figure 22:
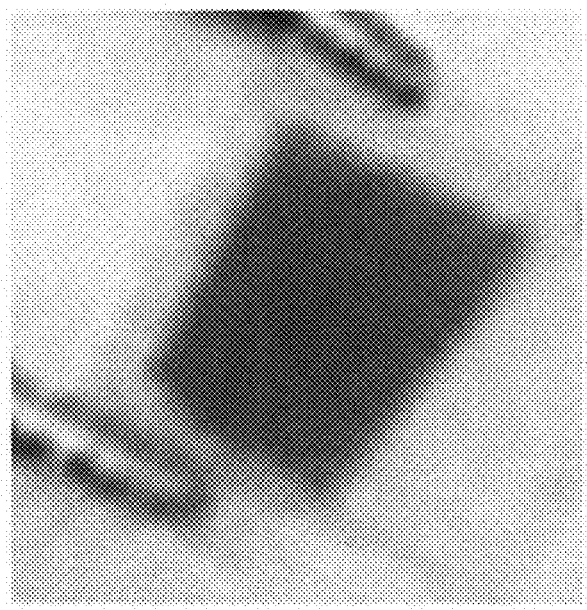

FIG. 22 shows that the electrochromic device according to the present example expresses bluish green. The electrochromic device shows an operating voltage ("x") of about 0.9 V ($0.9 \leq x \leq 1.1$), and a potential window of about 0.9 to about 1.5 V.

Example 10

Synthesis of a Compound of Chemical Formula 3D

A 0.266 g (1 mmol) amount of 1,1-bis(4-aminophenyl)cyclohexane and 0.716 g (2 mmol) of 4-(2,4-dinitrophenyl)-4,4'-dipyridyl are refluxed in 200 mL of ethanol for 5 days. The solvent is removed to obtain a yellow solid. The yellow solid is dissolved in a minimum quantity of methanol followed by the addition of acetone until precipitation. The precipitate is filtered, washed several times with acetone, and dried in an oven at 70° C. The synthesis is shown in Chemical Reaction Schemes 12 and 13.

Chemical Reaction Scheme 12

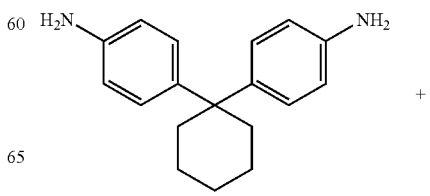

-continued

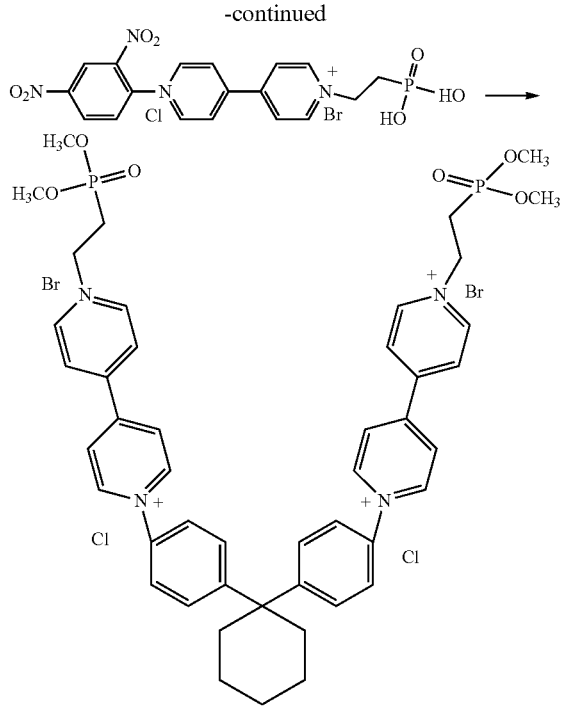

Chemical Reaction Scheme 13

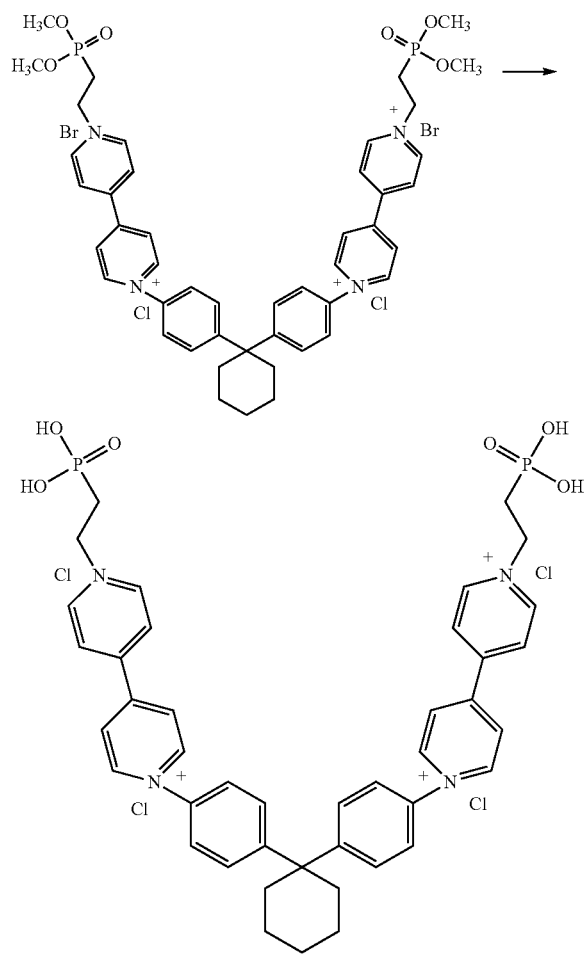

Figure 6:
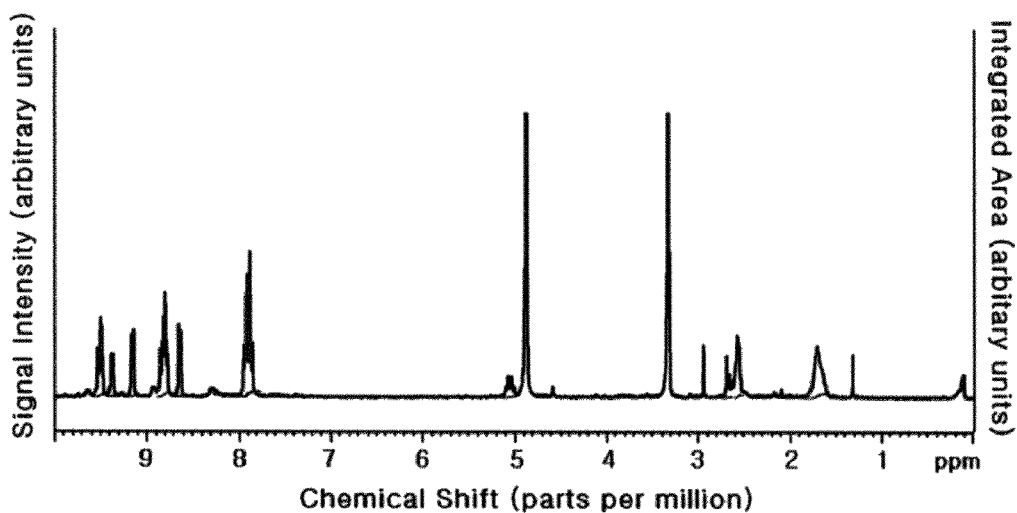

The molecular structure of the compound is confirmed by the $^1$H NMR spectrum shown in FIG. 6. It is confirmed that a phosphonic acid group is attached to two pyridyl (viologen) moieties.

Fabrication of Electrochromic Device and Measurement of Electrical Characteristics The electrochromic device is fabricated according to the same method as in Example 1, except that the compound prepared in Example 10 is used instead of the compound of Example 1, and the voltage is applied to the electrochromic device to measure electrochromism.

Figure 23:
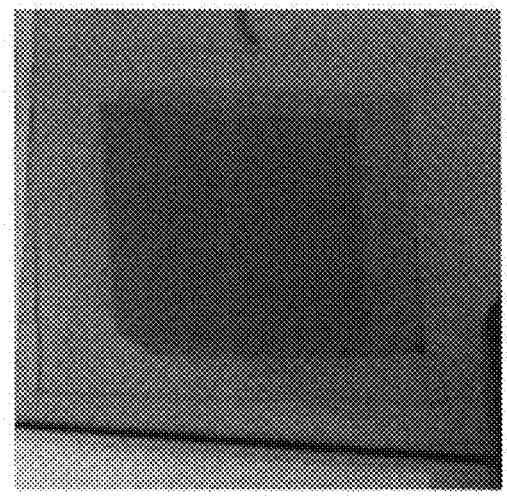

FIG. 23 shows that the electrochromic device according to the present example expresses green. The electrochromic device shows an operating voltage ("x") of about 0.9 V ($0.9 \leq x \leq 1.1$), and a potential window of about 0.9 to about 1.6 V.

Example 11

Synthesis of a Compound of Chemical Formula 3E

A compound represented by Chemical Formula 3E is obtained according to the same method as in Example 7, except that 4'-bromomethyl 4-phenyl benzonitrile is used instead of 4-(2,4-dinitrophenyl)-4'-(ethyl-diethyl phosphonate)-4,4'-dipyridyl.

Chemical Formula 3E

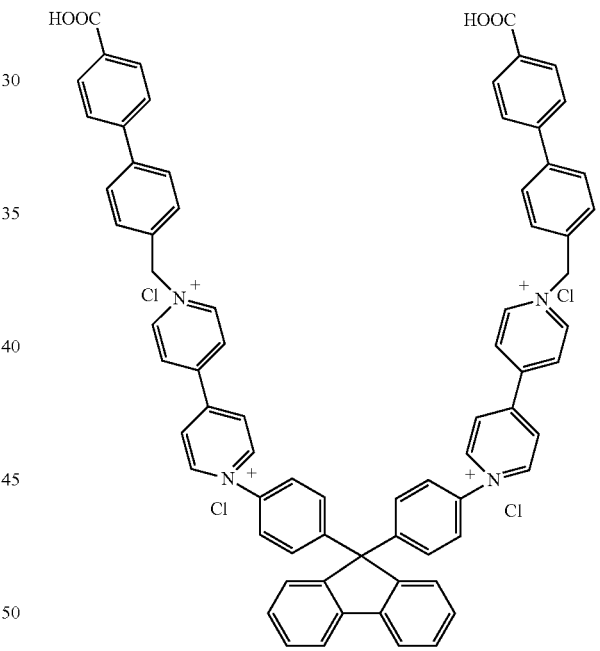

Figure 7:
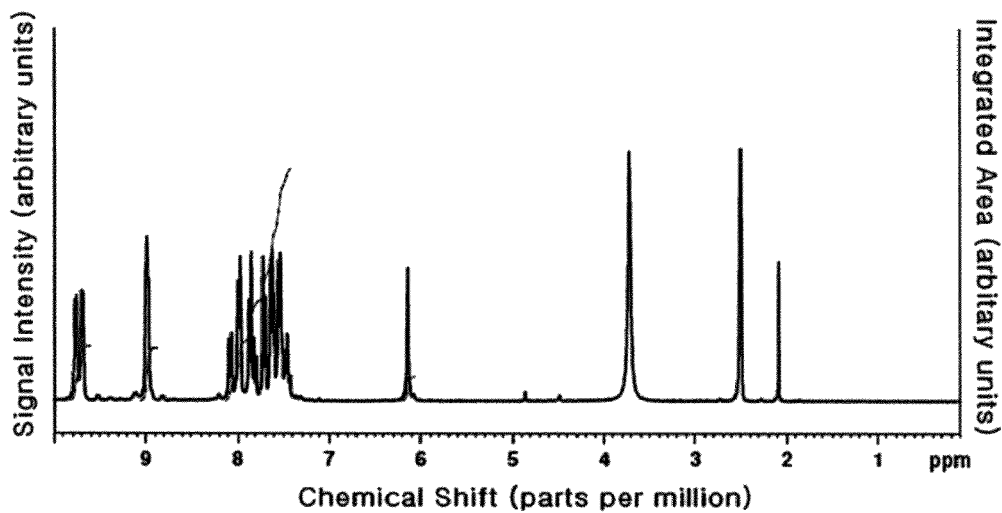

The molecular structure of the compound is confirmed by the $^1$H NMR spectrum shown in FIG. 7. It is confirmed that a carboxylic acid group is attached to two pyridyl (viologen) moieties.

Fabrication of Electrochromic Device and Measurement of Electrical Characteristics The electrochromic device is fabricated according to the same method as in Example 1, except that the compound prepared in Example 11 is used instead of the compound of Example 1, and the voltage is applied to the electrochromic device to measure electrochromism.

Figure 24:
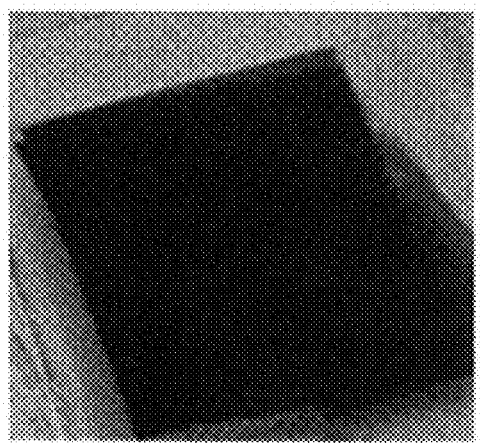

FIG. 24 shows that the electrochromic device according to the present example expresses green. The electrochromic device shows an operating voltage ("x") of about 0.9 V ($0.9 \leq x \leq 1.1$), and a potential window of about 0.9 to about 1.6 V.

Example 12

Synthesis of a Compound of Chemical Formula 3F

A 0.356 g (1 mmol) amount of 4-(ethyl diethyl phosphonate)-4,4'-dipyridinium chloride and 2,6-di(bromomethyl)-pyridine are refluxed in acetonitrile for 7 days. The solvent was evaporated under reduced pressure to obtain a yellow-brown solid. This is treated with hot acetonitrile and filtered followed by precipitation with a solution of methanol and acetone to obtain a brownish yellow solid, as shown in Chemical Reaction Scheme 14.

Chemical Reaction Scheme 14

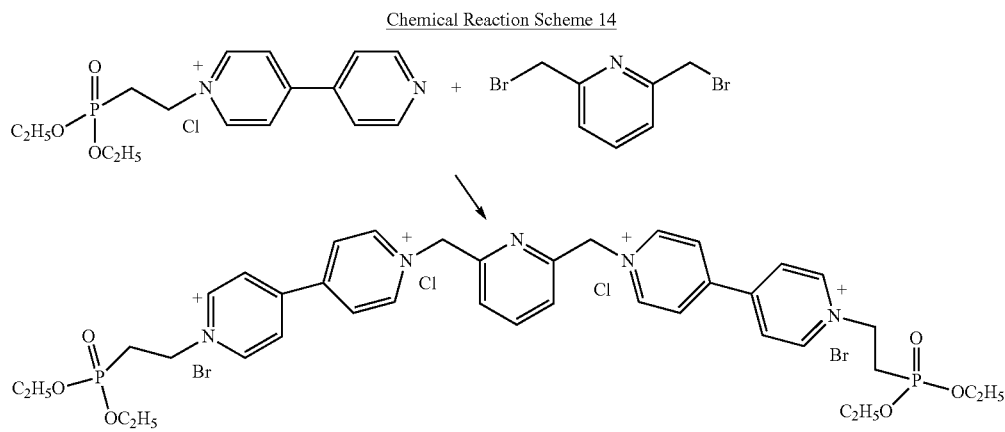

The solid is then refluxed in 80 mL of 35% hydrochloric acid for one day. The reaction mixture is evaporated followed by acetone treatment. The resultant yellow colored residue is filtered and is dissolved in methanol. Next, the resulting precipitate is filtered using acetone to obtain the compound of Chemical Formula 3F as shown in Chemical Reaction Scheme 15.

Chemical Reaction Scheme 15

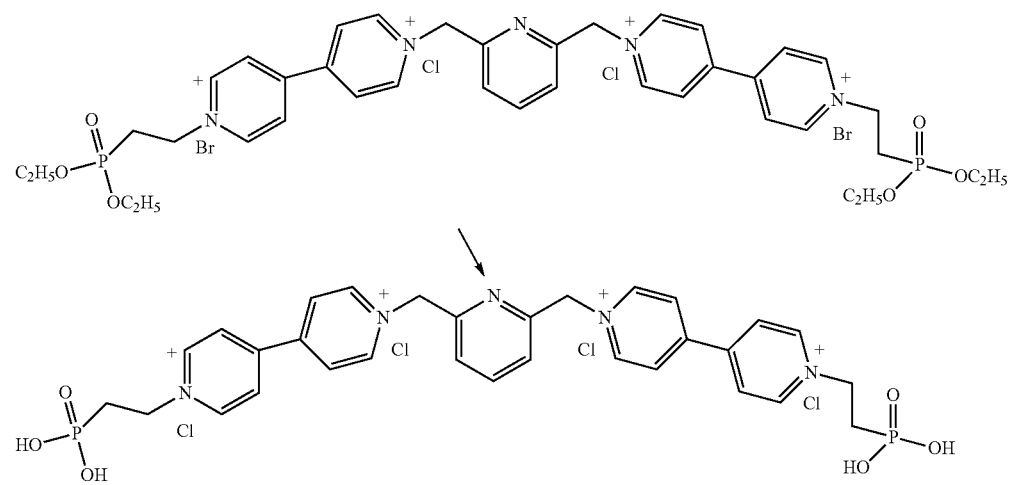

Figure 8:
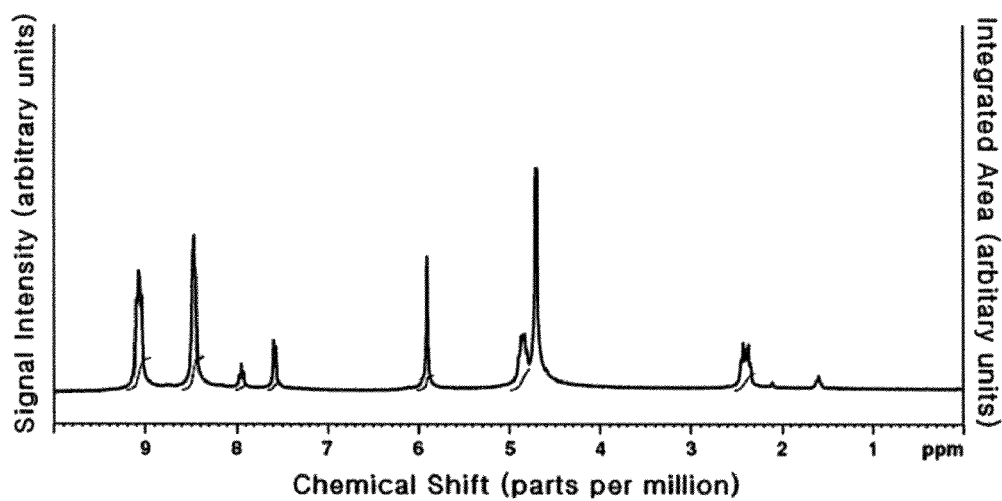

The molecular structure of the compound is confirmed by the $^1$H NMR spectrum shown in FIG. 8. It is confirmed that a phosphonic acid group is attached to two pyridyl (viologen) moieties.

Fabrication of Electrochromic Device and Measurement of Electrical Characteristics The electrochromic device is fabricated according to the same method as in Example 1, except that the compound prepared in Example 12 is used instead of the compound of Example 1, and the voltage is applied to the electrochromic device to measure electrochromism.

Figure 25:
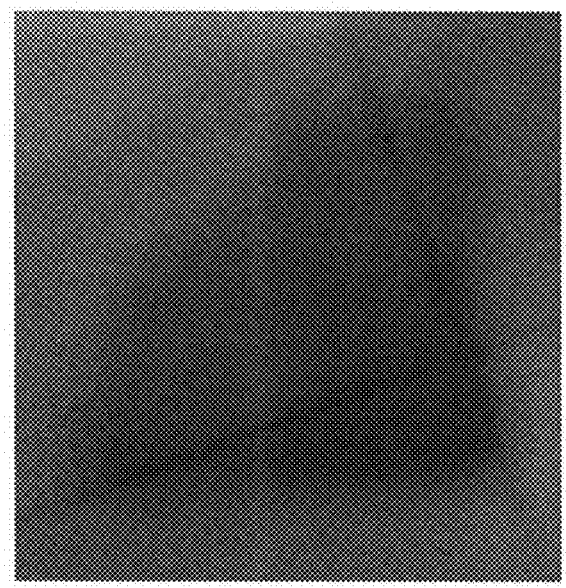

FIG. 25 shows that the electrochromic device according to the present example expresses bluish green. The electrochromic device shows an operating voltage ("x") of about 0.9 V ($0.9 \leq x \leq 1.1$), and a potential window of about 0.9 to about 1.5 V.

Example 13

Mixture Preparation

The compound of Chemical Formula 3C in Example 9 and the compound of Chemical Formula 3F in Example 12 are mixed to obtain a mixture.

The compound of Chemical Formula 3C is a green-expressing electrochromic compound, and the compound of Chemical Formula 3F is a bluish violet-expressing electrochromic compound.

Fabrication of Electrochromic Device and Measurement of Electrical Characteristics The electrochromic device is fabricated according to the same method as in Example 1, except that the mixture prepared in Example 13 is used instead of the compound of Example 1, and the voltage is applied to the electrochromic device to measure electrochromism.

Figure 26:
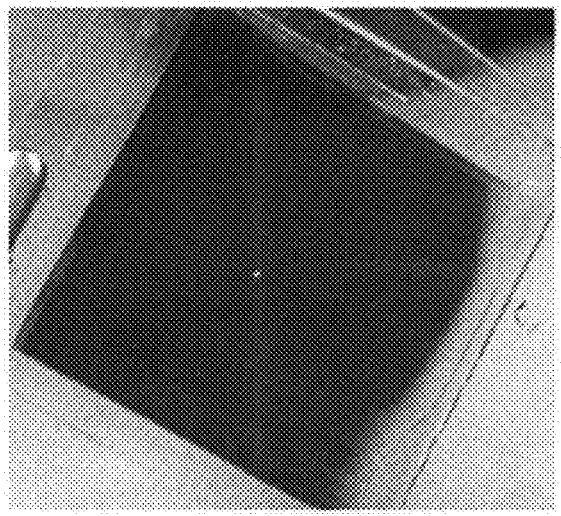

FIG. 26 shows that the electrochromic device according to the present example expresses deep violet. The electrochromic device shows an operating voltage ("x") of about 0.9 V ($0.9 \leq x \leq 1.1$), and a potential window of about 0.9 to about 1.5 V.

Example 14

Fabrication of Black Electrochromic Material

The compound of Chemical Formula 3C in Example 9, the compound of Chemical Formula 3F in Example 12, and a red electrochromic compound are mixed to obtain a mixture.

The compound of Chemical Formula 3C is a green-expressing electrochromic compound, and the compound of Chemical Formula 3F is violet-expressing electrochromic compound.

Fabrication of Electrochromic Device and Measurement of Electrical Characteristics The electrochromic device is fabricated according to the same method as in Example 1, except that the mixture prepared in Example 14 is used instead of the compound of Example 1, and the voltage is applied to the electrochromic device to measure electrochromism.

Figure 27:
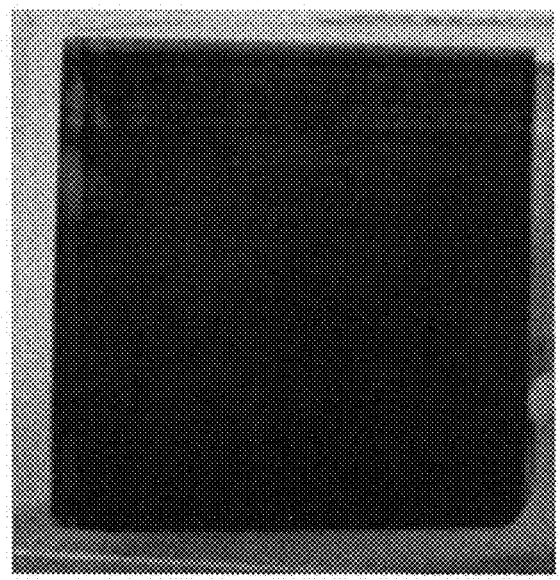

FIG. 27 shows that the electrochromic device according to the present example expresses black. The electrochromic device shows an operating voltage ("x") of about 0.9 V ($0.9 \leq x \leq 1.1$), and a potential window of about 0.9 to about 1.8 V.

Comparative Example

Synthesis of Viologen Compound Having Another Structure

The electrochromic compound is synthesized according to Example 1 of International Patent Laid-Open Publication No. 2004-067673 (WO 2004/067673).

The electrochromic device is fabricated according to the same method as in Example 1, except that the compound prepared in the Comparative Example is used instead of the compound of Example 1, and the voltage is applied to the electrochromic device to measure electrochromism.

The electrochromic device according to the comparative example shows electrochromism at 0.5 V, and maintains the same color up to about 0.9 V.

Measurement of Electrical Characteristics of Electrochromic Devices

The electrical characteristics of the electrochromic devices were measured.

The results are shown in FIGS. 9 to 15 and Table 1.

Figure 9:
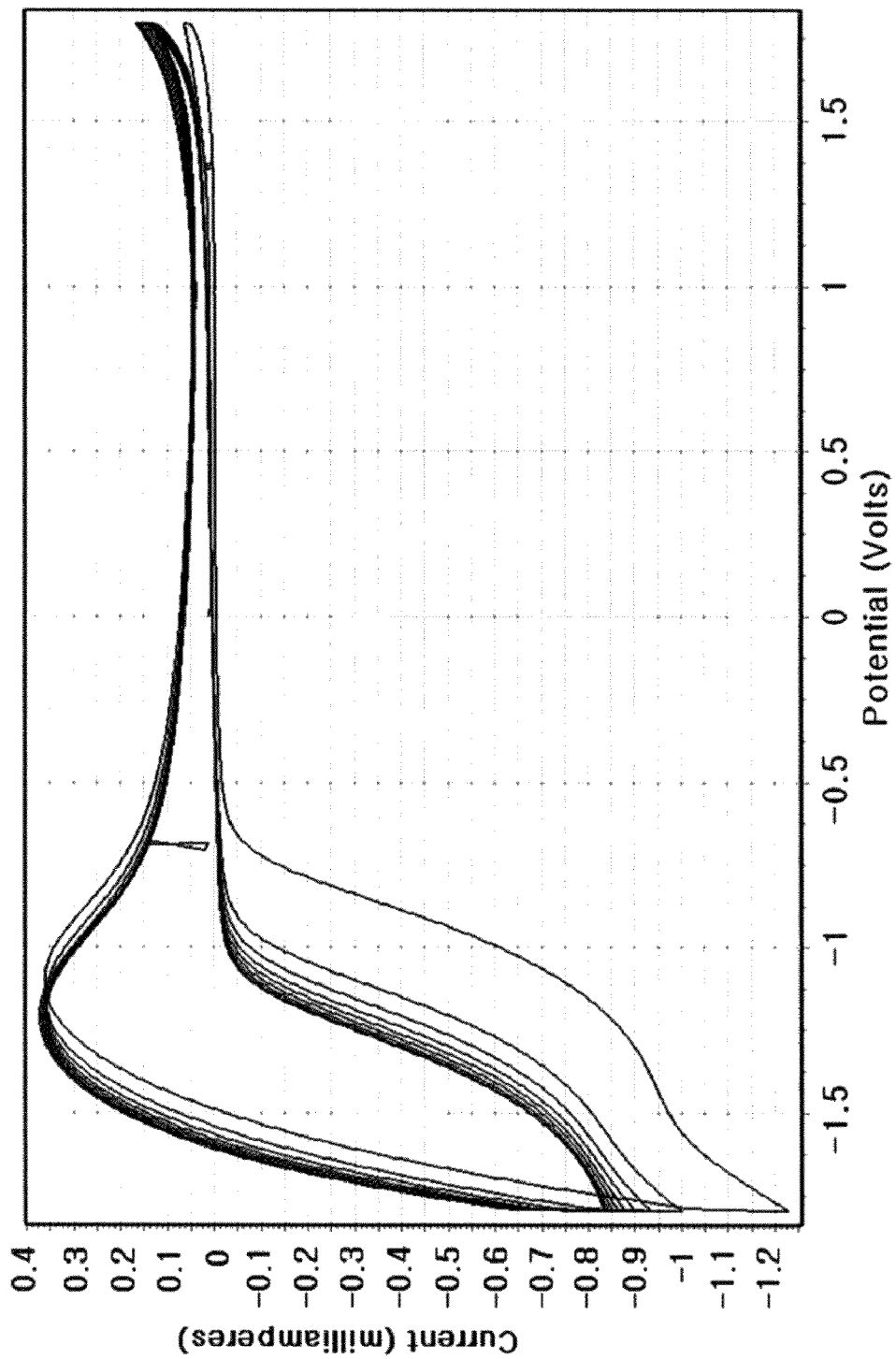
FIGS. 9 to 11 are cyclic voltammograms and illustrate current (amperes) versus potential (volts) of electrochromic devices including the electrochromic materials according to Examples 4, 9, and 10, respectively.
Figure 10:
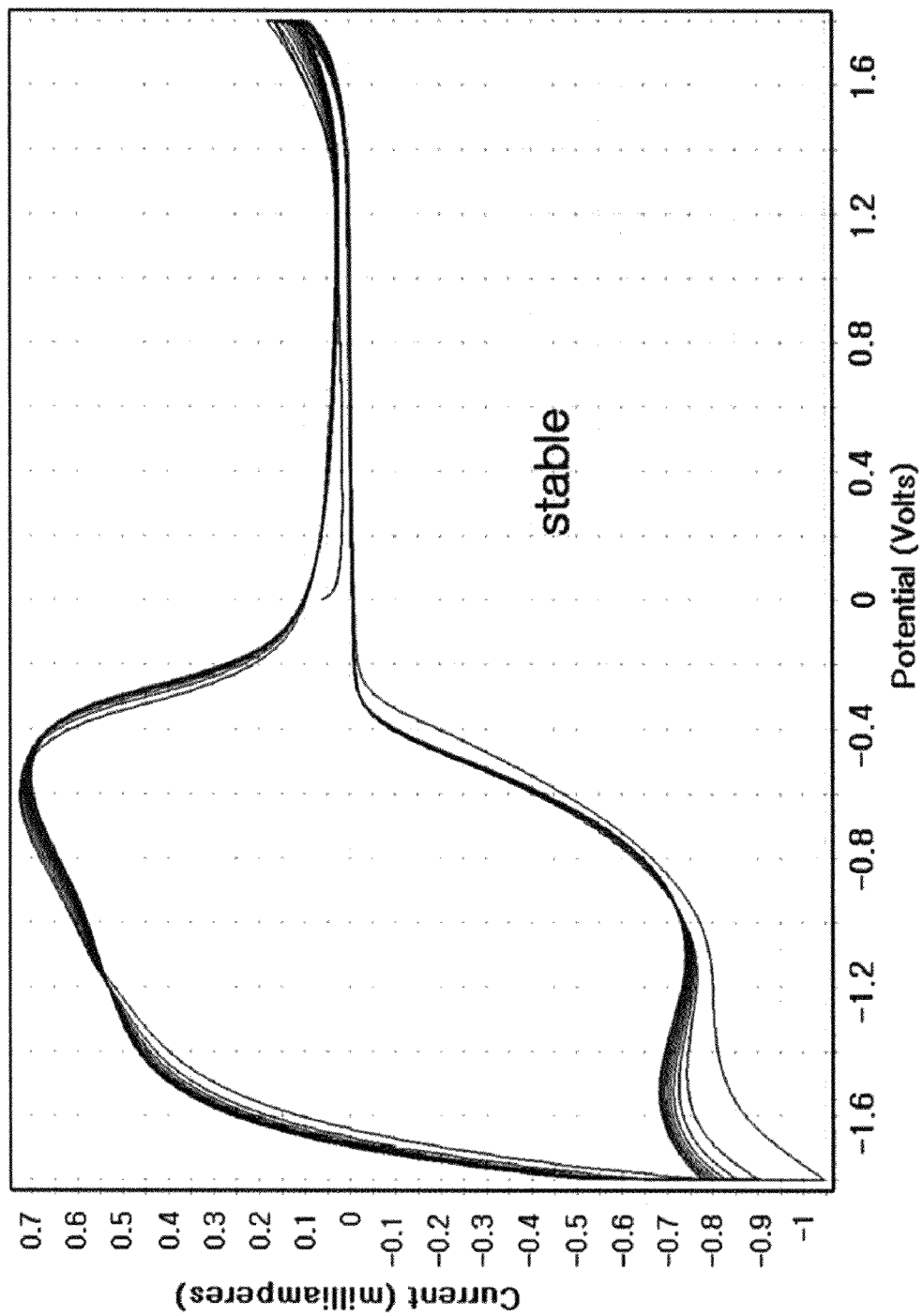
Figure 11:
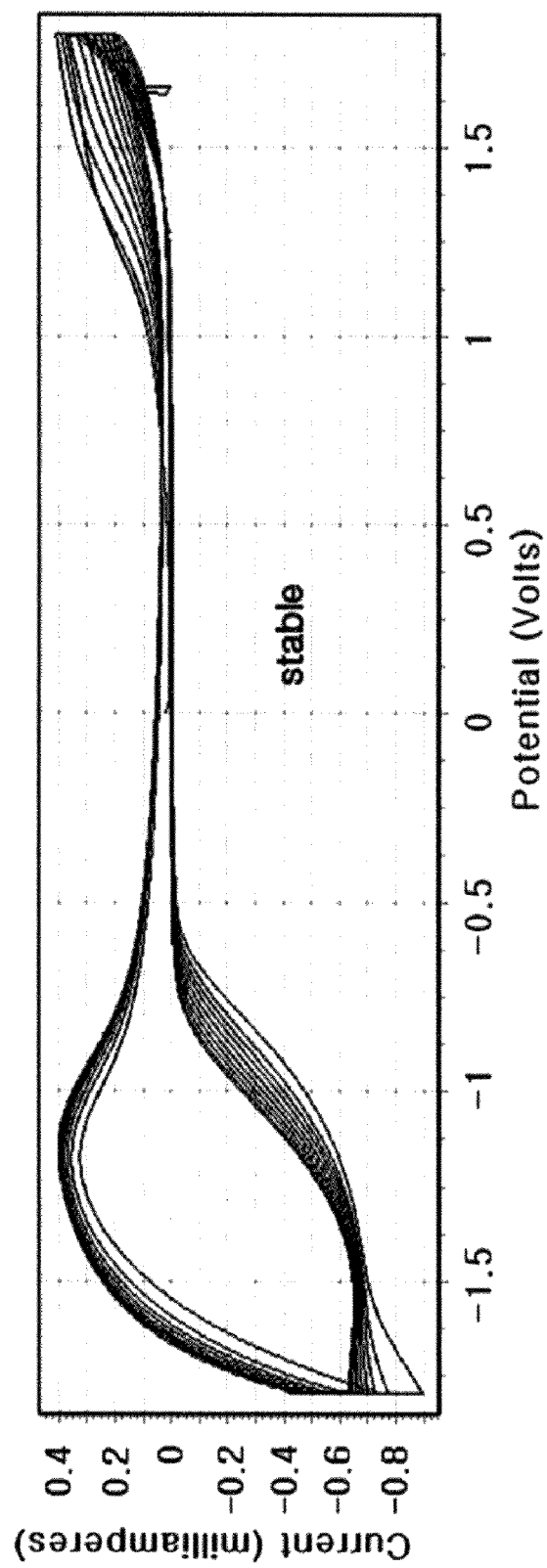
Figure 12:
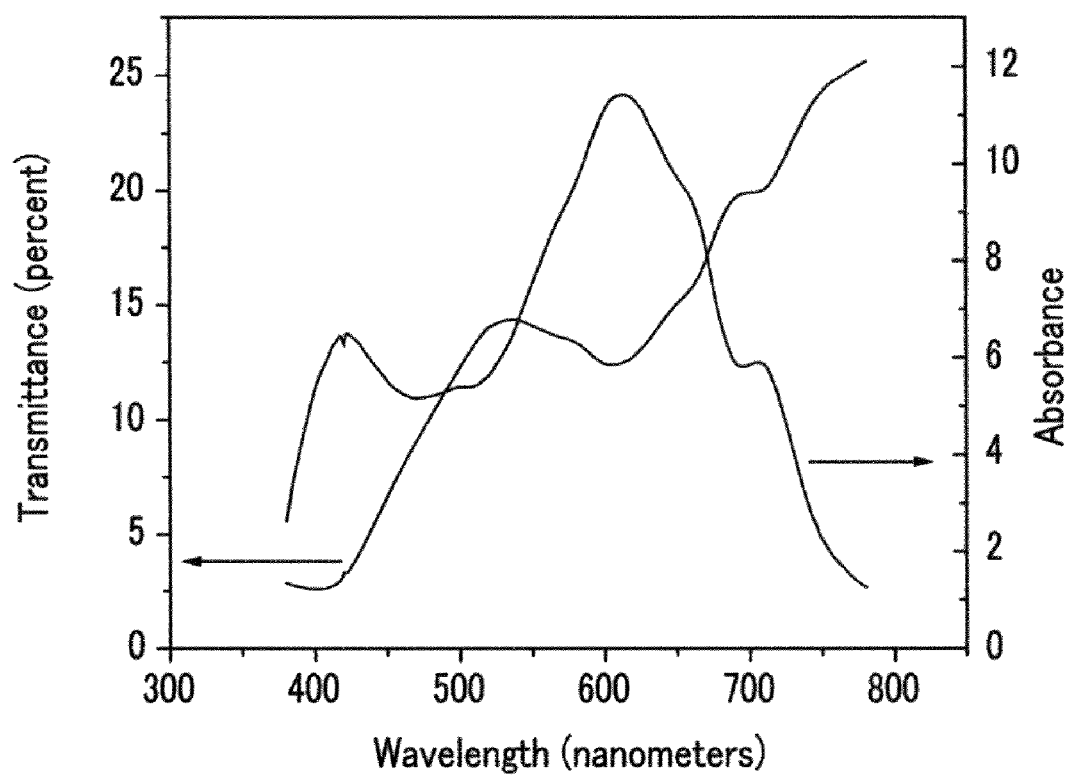
FIGS. 12 to 13 are graphs illustrating transmittance (percent) and absorbance (percent) versus wavelength (nanometers) of electrochromic devices including the electrochromic materials according to Examples 9 and 12, respectively.
Figure 13:
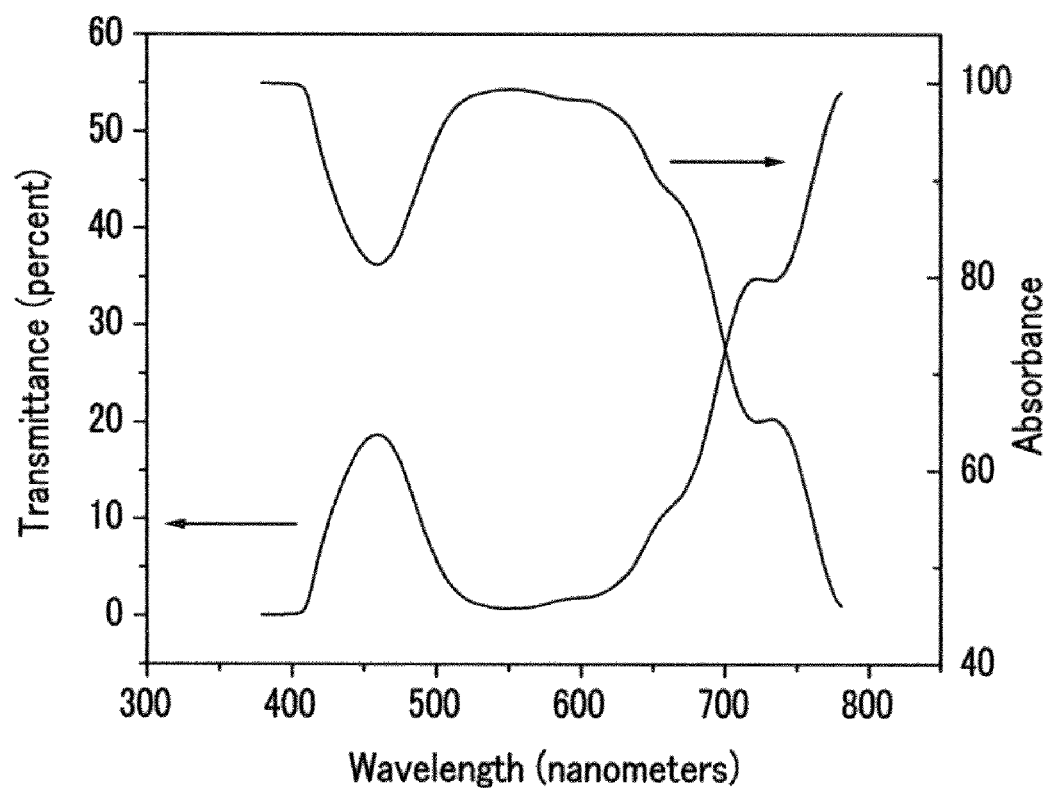
Figure 14:
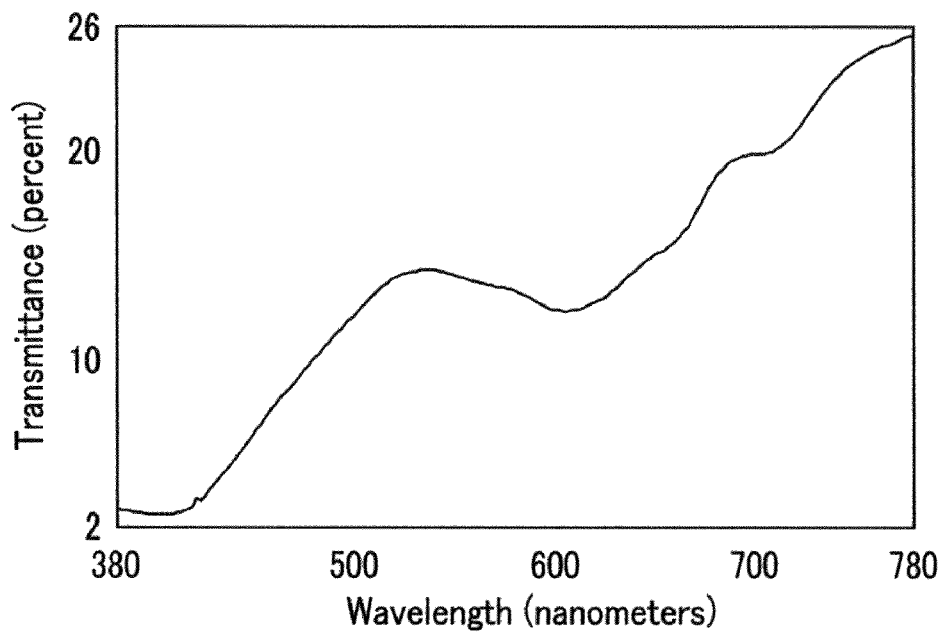
FIG. 14 is a graph illustrating transmittance (percent) versus wavelength (nanometers) of an electrochromic device including the electrochromic material according to Example 14.
Figure 15:
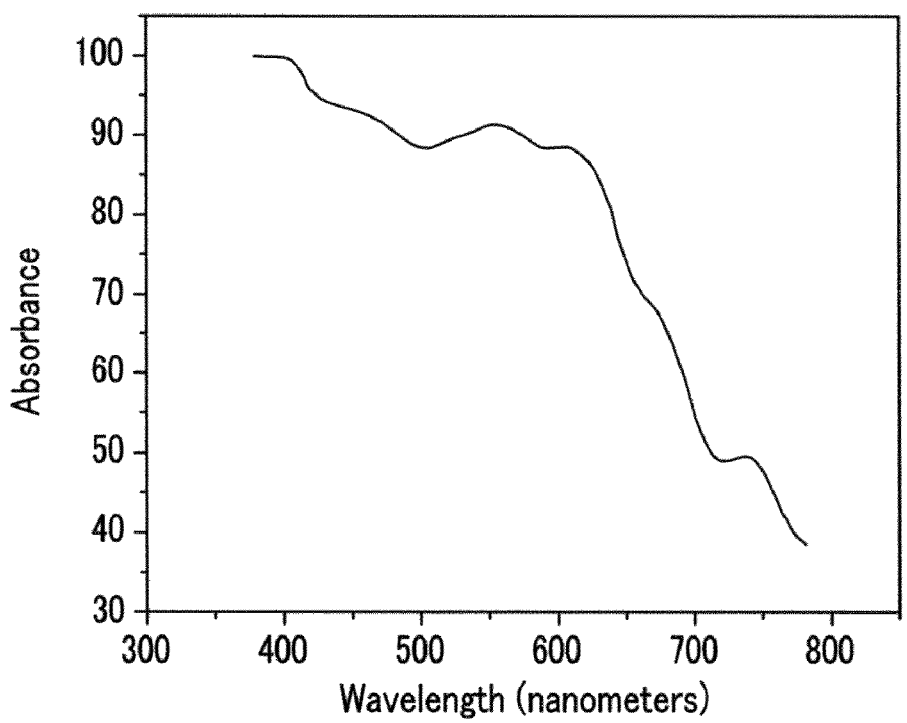
FIG. 15 is a graph illustrating absorbance (percent) versus wavelength (nanometers) of an electrochromic device including the electrochromic material according to Example 14.

FIGS. 9 to 11 are graphs showing cyclic voltammograms of the electrochromic devices including the electrochromic materials according to Examples 4, 9, and 10, respectively, and FIGS. 12 to 13 are graphs showing wavelengths of colors expressed by the electrochromic device including the electrochromic materials according to Examples 9 and 12, respectively, and FIGS. 14 to 15 are graphs showing wavelengths of colors expressed by the electrochromic device including the electrochromic material according to Example 14.

Referring to FIGS. 9 to 11, the electrochromic device according to Examples 4, 9, and 12 show uniform peak potential and current when cycled in a selected voltage range ten times, indicating that the electrochemical stability of the oxidized and reduced states is good.

Referring to FIGS. 12 and 13, the electrochromic materials according to Examples 9 and 12 express green and violet color, respectively. Referring to FIGS. 14 and 15, the electrochromic materials according to Example 14 express black.

The operating voltages and potential window ranges of the electrochromic devices are shown in Table 1.

Table 1 shows operating voltages and potential window ranges of electrochromic compounds according to Examples 1 to 14 and the comparative example.

TABLE 1

|  | Operating voltage (V) | Potential window (V) |
| --- | --- | --- |
| Example 1 | $0.9 \leq x \leq 1.1$ | 0.9-1.6 |
| Example 2 | $0.8 \leq x \leq 1.1$ | 0.8-1.5 |
| Example 3 | $0.9 \leq x \leq 1.1$ | 0.9-1.6 |
| Example 4 | $0.9 \leq x \leq 1.1$ | 0.9-1.5 |
| Example 5 | $0.9 \leq x \leq 1.1$ | 0.9-1.6 |
| Example 6 | $0.8 \leq x \leq 1.1$ | 0.8-2.1 |
| Example 7 | $0.9 \leq x \leq 1.1$ | 0.9-1.8 |
| Example 8 | $0.9 \leq x \leq 1.1$ | 0.9-1.5 |
| Example 9 | $0.9 \leq x \leq 1.1$ | 0.9-1.5 |
| Example 10 | $0.9 \leq x \leq 1.1$ | 0.9-1.6 |
| Example 11 | $0.9 \leq x \leq 1.1$ | 0.9-1.6 |
| Example 12 | $0.9 \leq x \leq 1.1$ | 0.9-1.5 |
| Example 13 | $0.9 \leq x \leq 1.1$ | 0.9-1.5 |
| Example 14 | $0.9 \leq x \leq 1.1$ | 0.9-1.8 |
| Comparative example | 0.5 | 0.5-0.9 |

Referring to Table 1, the electrochromic materials according to the Examples show an operating voltage ("x") of about 0.9 V or more. The green electrochromic device and dark blue or violet electrochromic devices shows a potential window of about 1 to about 1.5 V, and the black electrochromic device shows a potential window of about 1 to about 1.8 V.

As described, the electrochromic materials according to the Examples show increased operating voltage and a higher potential window compared with that of the comparative example. Thus, electrochromic devices having excellent stability and reliability may be provided.

While this disclosure has been described in connection with exemplary embodiments, it is to be understood that the disclosure is not limited to the particular embodiments disclosed as the best mode contemplated for carrying out this disclosure, but, on the contrary, is intended to cover various modifications and equivalent arrangements included within the spirit and scope of the appended claims.

What is claimed is:

1. An electrochromic material, comprising:
at least one compound represented by Chemical Formulas 1 to 3:

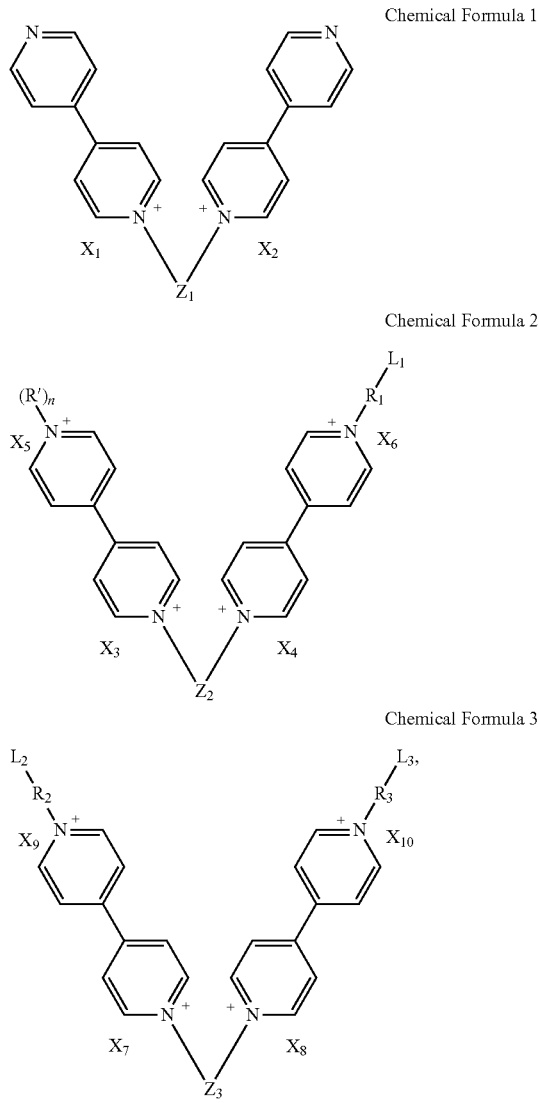

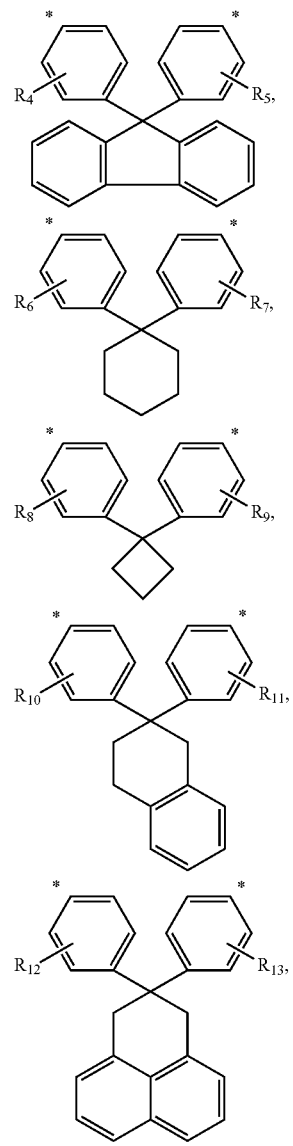

wherein $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group, a hydroxyl group or a combination thereof, $X_1$ to $X_{10}$ are each independently a halogen group, a halogen-containing group or a combination thereof, and $Z_1$ to $Z_3$ are each independently a radical of Chemical Formula A:

wherein $R_4$ to $R_{13}$ are each independently selected from hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group, a halogen group, a halogen-containing group or a combination thereof, and * represents a point of attachment.

2. The electrochromic material of claim 1, wherein the compound expresses green.

3. The electrochromic material of claim 1, wherein
the compound represented by Chemical Formula 1 comprises at least one compound of Chemical Formulas 1A to 1C,
the compound represented by Chemical Formula 2 comprises at least one compound of Chemical Formulas 2A to 2C, and
the compound represented by Chemical Formula 3 comprises at least one compound of Chemical Formulas 3A to 3E:

Chemical Formula 1A
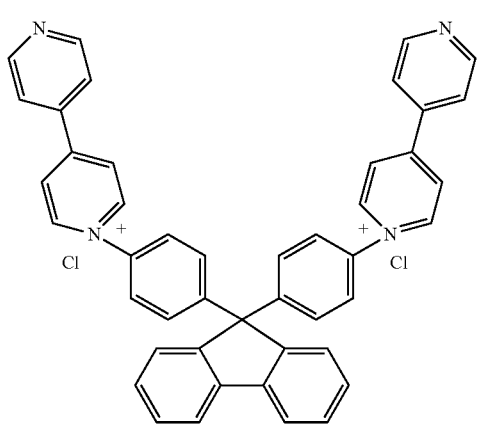
Chemical Formula 1B
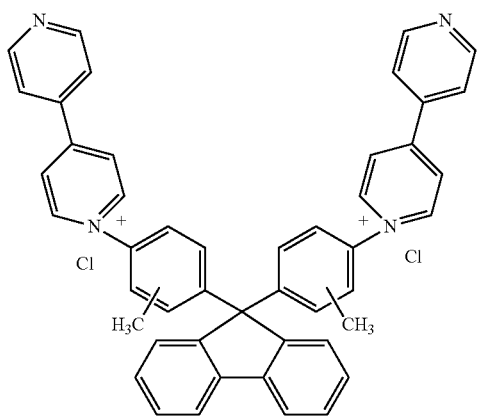
Chemical Formula 1C
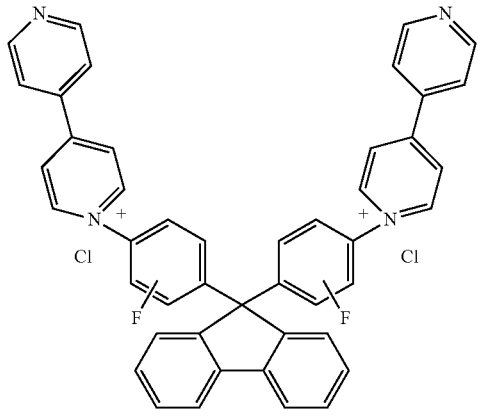
Chemical Formula 2A
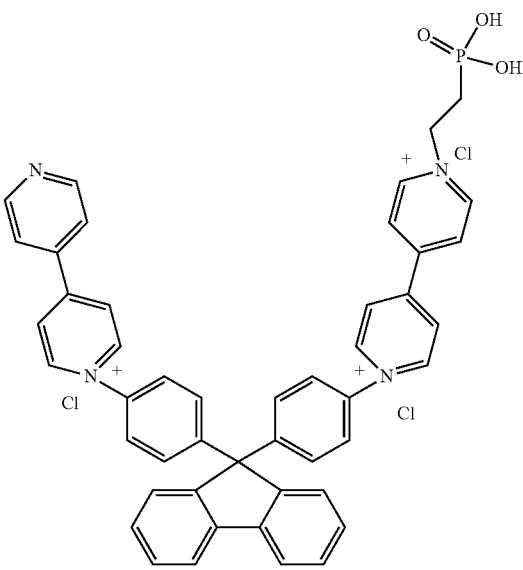
Chemical Formula 2B
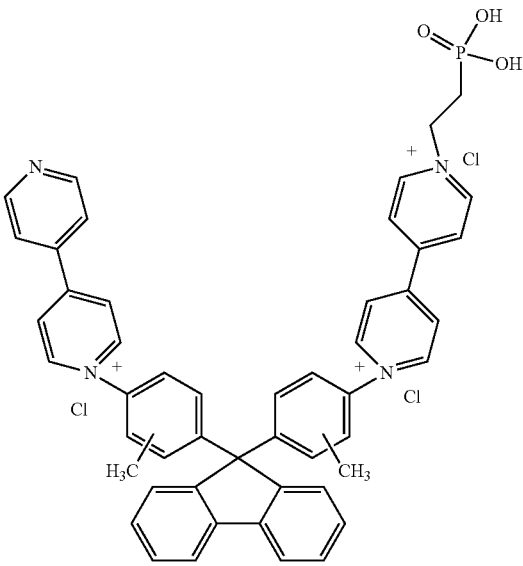

Chemical Formula 2C
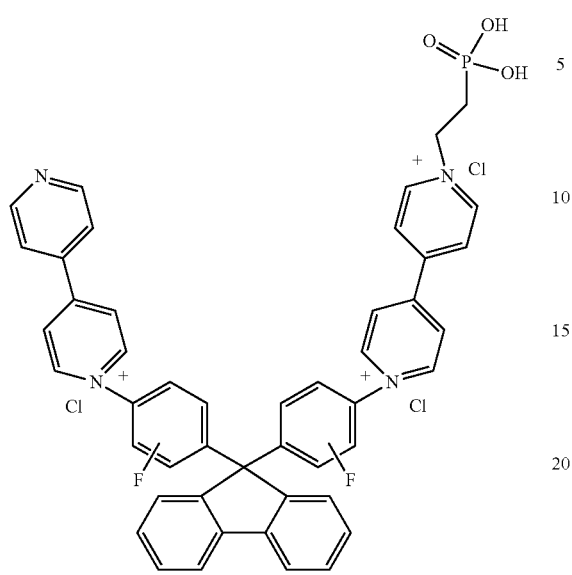
Chemical Formula 3A
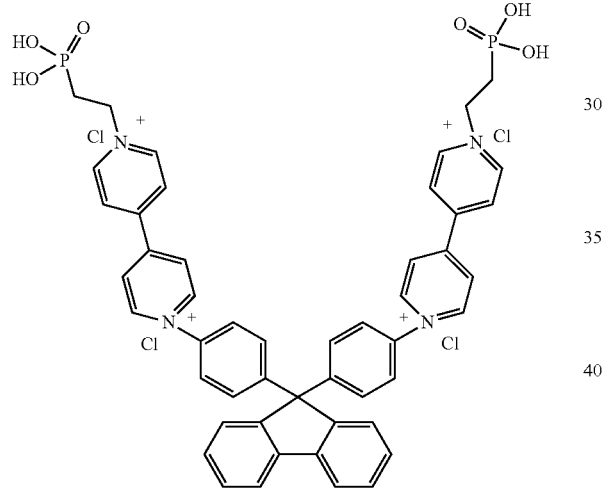
Chemical Formula 3B
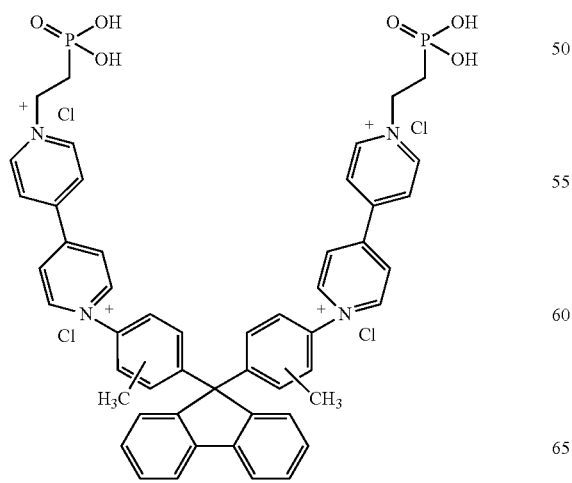
Chemical Formula 3C
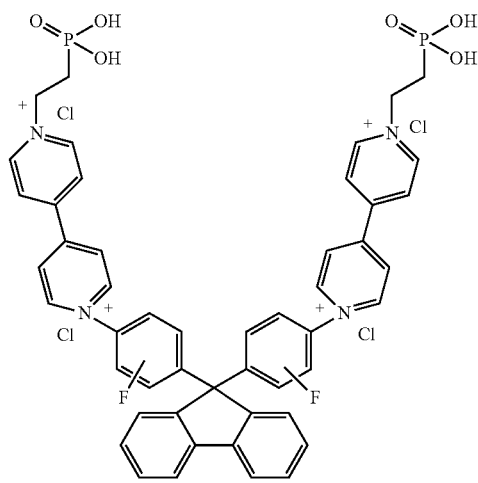
Chemical Formula 3D
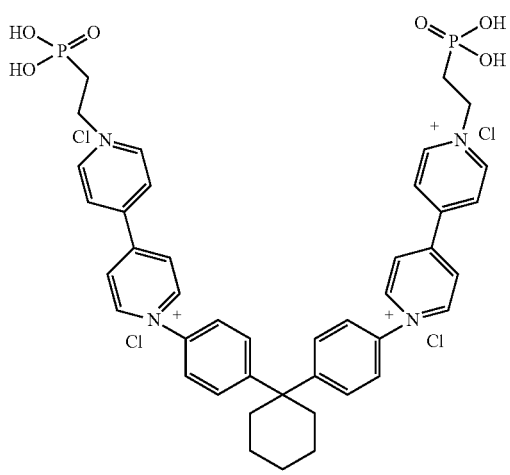
Chemical Formula 3E
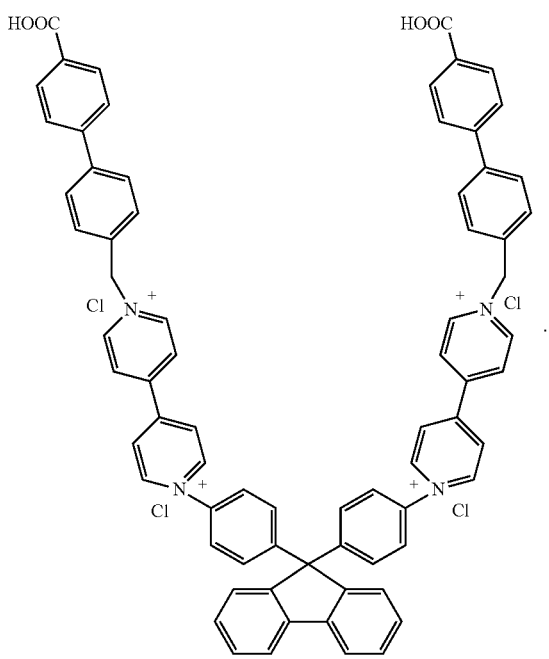

4. The electrochromic material of claim 1,
further comprising at least one compound of Chemical Formulas 1 to 3,
wherein $R_1$ to $R_3$, R', n, $L_1$ to $L_3$, and $X_1$ to $X_{10}$ are as defined in claim 2, and $Z_1$ to $Z_3$ are each independently represented by Chemical Formula B:

$$-R_{14}-Y-R_{15}-, \quad \text{Chemical Formula B}$$

wherein Y is a $C_2$ to $C_{20}$ heteroarylene group, which includes at least one nitrogen, and $R_{14}$ and $R_{15}$ are independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

5. The electrochromic material of claim 4, wherein the electrochromic material further comprises a compound expressing a red color.

6. An electrochromic material, comprising:
at least one compound represented by Chemical Formulas 1 to 3:

Chemical Formula 1

Chemical Formula 2

Chemical Formula 3 wherein $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group, a hydroxyl group or a combination thereof, $X_1$ to $X_{10}$ are each independently a halogen group, a halogen-containing group or a combination thereof, and $Z_1$ to $Z_3$ are each independently represented by Chemical Formula B:

Chemical Formula B wherein Y is a $C_2$ to $C_{20}$ heteroarylene group, which includes at least one nitrogen, and $R_{14}$ and $R_{15}$ are each independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

7. The electrochromic material of claim 6, wherein Y is selected from the group of radicals represented by Chemical Formula C:

Chemical Formula C

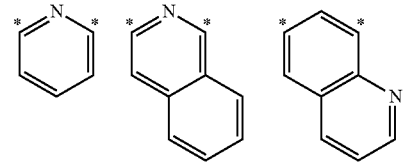

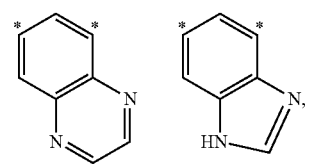

in which * represents a point of attachment.

8. The electrochromic material of claim 6, wherein the compound expresses a dark blue color or violet color.

9. The electrochromic material of claim 6, wherein the electrochromic material comprises a compound represented by Chemical Formula 3F:

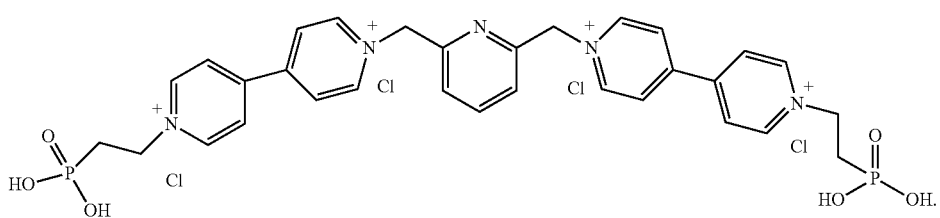

Chemical Formula 3F

10. An electrochromic device, comprising:
a first electrode;
a second electrode facing the first electrode;
an electrochromic material disposed on the first electrode or the second electrode; and
an electrolyte layer interposed between the first electrode and the second electrode,
wherein the electrochromic material comprises at least one electrochromic compound represented by Chemical Formulas 1 to 3:

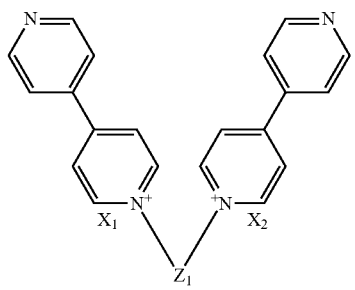

Chemical Formula 1

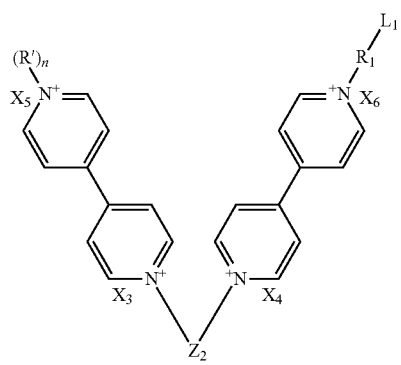

Chemical Formula 2

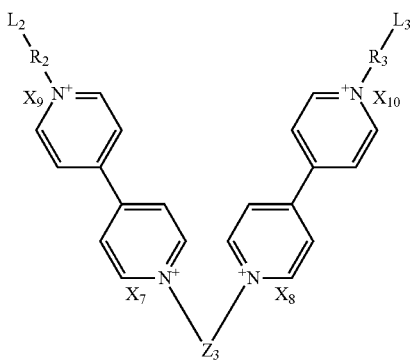

Chemical Formula 3 wherein $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group or a hydroxyl group, $X_1$ to $X_{10}$ are each independently a halogen group, a halogen-containing group or a combination thereof, and $Z_1$ to $Z_3$ are each independently a radical of Chemical Formula A:

Chemical Formula A

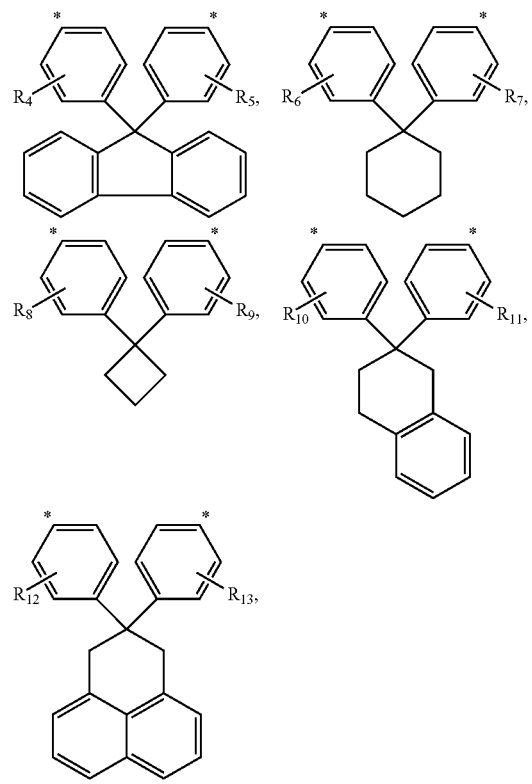

wherein $R_4$ to $R_{13}$ are each independently selected from hydrogen, a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group, a halogen group, a halogen-containing group or a combination thereof.

11. The electrochromic device of claim 10, wherein the electrochromic device has a potential window of about 1.0 Volts to about 1.5 Volts.

12. The electrochromic device of claim 10, wherein the electrochromic material further comprises
at least one electrochromic compound represented by Chemical Formulas 1 to 3, wherein
$R_1$ to $R_3$, R', n, $L_1$ to $L_3$, and $X_1$ to $X_{10}$ are as defined in claim 12, and $Z_1$ to $Z_3$ are each independently represented by Chemical Formula B:

—$R_{14}$—Y—$R_{15}$—, Chemical Formula B wherein Y is a $C_2$ to $C_{20}$ heteroarylene group, which includes at least one nitrogen, and $R_{14}$ and $R_{15}$ are each independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

13. The electrochromic device of claim 12, wherein the electrochromic material further comprises an electrochromic compound expressing red color.

14. The electrochromic device of claim 13, wherein the electrochromic device has a potential window of about 0.9 Volts to about 1.8 volts.

15. The electrochromic device of claim 10, wherein the electrochromic device has an operating voltage of equal to or greater than about 0.9 volts.

16. An electrochromic device, comprising:
a first electrode;
a second electrode facing the first electrode;
an electrochromic material disposed on the first electrode or the second electrode; and
an electrolyte later interposed between the first electrode and the second electrode,
wherein the electrochromic material comprises at least one electrochromic compound represented by Chemical Formulas 1 to 3:

Chemical Formula 1

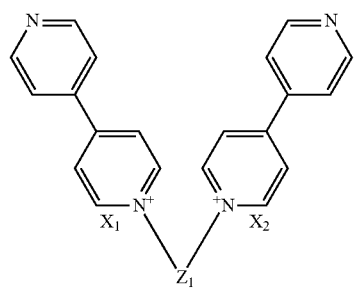

Chemical Formula 2

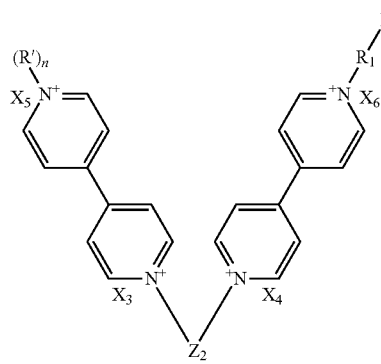

Chemical Formula 3

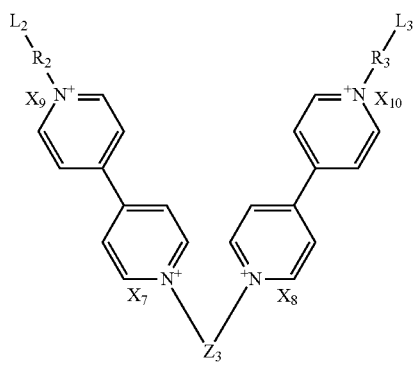

wherein $R_1$ to $R_3$ are each independently selected from a single bond, a substituted or unsubstituted $C_1$ to $C_{30}$ alkylene group, a substituted or unsubstituted $C_3$ to $C_{30}$ cycloalkylene group, a substituted or unsubstituted $C_6$ to $C_{30}$ arylene group, a substituted or unsubstituted $C_2$ to $C_{30}$ heteroarylene group or a combination thereof, R' is selected from a substituted or unsubstituted $C_1$ to $C_{30}$ alkyl group, a substituted or unsubstituted $C_3$ to $C_{30}$ cycloalkyl group, a substituted or unsubstituted $C_6$ to $C_{30}$ aryl group, a substituted or unsubstituted $C_2$ to $C_{30}$ heteroaryl group or a combination thereof, n is 0 or 1, $L_1$ to $L_3$ are each independently selected from a phosphonic acid group, a carboxylic acid group, a sulfonic acid group or a hydroxyl group, $X_1$ to $X_{10}$ are each independently a halogen group, a halogen-containing group or a combination thereof, and $Z_1$ to $Z_3$ are each independently represented by Chemical Formula B:

—$R_{14}$—Y—$R_{15}$—, Chemical Formula B wherein Y is a $C_2$ to $C_{20}$ heteroarylene group, which includes at least one nitrogen, and $R_{14}$ and $R_{15}$ are each independently selected from a single bond, a substituted or unsubstituted $C_1$ to $C_{30}$ alkylene group, a substituted or unsubstituted $C_3$ to $C_{30}$ cycloalkylene group, a halogen group, a halogen-containing group or a combination thereof.

17. The electrochromic device of claim 16, wherein Y is selected from the group of radicals represented by Chemical Formula C:

Chemical Formula C

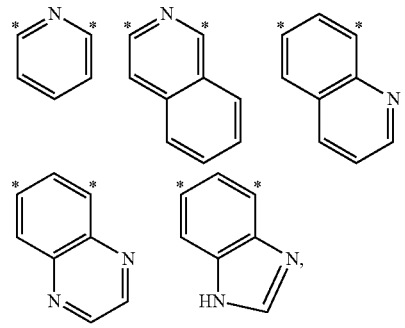

in which * represents a point of attachment.

18. The electrochromic device of claim 16, wherein the electrochromic device has a potential window of about 0.9 Volts to about 1.8 Volts.

19. The electrochromic device of claim 16, wherein the electrochromic device has an operating voltage of equal to or greater than about 0.9 volts.

* * * * *